United States Patent [19]
Samal

[11] Patent Number: 5,874,399
[45] Date of Patent: Feb. 23, 1999

[54] PROGENITOR B CELL STIMULATING FACTOR

[75] Inventor: Babru Bahan Samal, Moorpark, Calif.

[73] Assignee: Amgen Inc., Thousand Oaks, Calif.

[21] Appl. No.: 448,735

[22] Filed: May 24, 1995

Related U.S. Application Data

[62] Division of Ser. No. 294,770, Aug. 23, 1994, Pat. No. 5,580,754, which is a continuation of Ser. No. 980,524, Nov. 20, 1992, abandoned.

[51] Int. Cl.⁶ .................................................. C07K 14/52
[52] U.S. Cl. ........................ 514/2; 530/351; 435/695; 435/252.3; 435/254.11; 435/325
[58] Field of Search .................... 530/350, 351; 435/69.1, 240.2, 252.3, 254.11, 69.5; 514/2

[56] References Cited

U.S. PATENT DOCUMENTS

| | | | |
|---|---|---|---|
| 4,179,937 | 12/1979 | Davis et al. | 435/18.1 |
| 4,710,473 | 12/1987 | Morris et al. | 435/320 |
| 4,965,195 | 10/1990 | Namen et al. | 435/69.52 |

FOREIGN PATENT DOCUMENTS

| | | |
|---|---|---|
| 0 225 579 A2 | 6/1987 | European Pat. Off. . |
| 8906541 | 7/1989 | WIPO . |
| WO89/06541 | 7/1989 | WIPO . |
| WO91/05795 | 5/1991 | WIPO . |

OTHER PUBLICATIONS

Aral et al. Ann Rev. Biochem. 59, 783 (1990).
Billips et al. Blood 79, 1185 (1992).
Brach et al. Acta. Haematol. 86, 128 (1991).
Chirgwin et al. Biochemistry 18, 5294 (1979).
Hodgson et al. Nature 281, 381 (1979).
Hunkapillar et al., Methods in Enzymol 91, 227 (1983).
Johnson et al. Dev. Biol. Stand. 69, 3 (1988).
Lehrach et al. Biochem. 16, 4743 (1977).
Liu et al. Biochem. 18 690 (1979).
Maniatis et al. Molecular Cloning, A Laboratory Manual (1988), 197–198, Cold Spring Harbor Laboratory, Cold Spring Harbor.
Martin et al. Cell 63 203 (1990).
May et al. PNAS 83, 8957 (1986).
McNiece et al. J. Immunol. 146, 3785 (1991).
Metcalf et al. Proc. natl. Acad. Sci. 88, 111310 (1991).
Migliaccio et al. J. Cell Physiol. 148, 503 (1991).
Miller et al. Biotechnique 7, 980 (1989).
Miller et al. Mol. Cell. Biol. 6 2895 (1986).
Nishida et al. Biochem. Biophys. Res. Commun. 143, 345 (1987).
Noonan et al. Nucleic Acid Res. 16, 10366 (1988).
Okayama et al. Methods Enzymol. 154 3 (1987).
Olofsson et al. Acta Oncol. 30, 889 (1991).
Ponting et al. Growth Factors 4, 165 (1991).
Remington Pharmaceutical Sciences (1990), 1519–1544, Mack Publishing Company, Easton, Pennsylvania.
Samal et al. Leuk. Res. 14, 575–580 (1990).
Sanger et al. PNAS 74, 5463 (1977).
Shaw et al. Cell 46, 659 (1986).
Taniguchi et al. Nature 302, 305 (1983).
Von Heljne et al. Nucleic Acid Res. 14, 4683 (1986).
Wong et al. Science 228, 810 (1985).
Yang et al. Cell. 47, 370 (1986)
Landreth et al., Blood 80, 1207–1212 (1992).
Landreth et al., Journal of Immunology 140, 845–852 (1988).
Namen et al., Journal Exp. Med. 167, 988–1002 (1988).
Woodward et al., Biological Abstracts 90(4), abstract no. 35798 (1990).

*Primary Examiner*—Sally P. Teng
*Attorney, Agent, or Firm*—Robert B. Winter; Steven M. Odre; Ron K. Levy

[57] ABSTRACT

A progenitor B cell stimulating factor which promotes the formation of pre-B cells is described. DNA sequences encoding same and methods of production and purification of the factor are also disclosed. The factor is used in the treatment of hematopoietic disorders and in bone marrow transplantation.

11 Claims, 16 Drawing Sheets

|     |     |     |     |     |     |     |     |     |     |     |     | GM | IL2 | IL1B | IL6 | IL3 |
| --- | --- | --- | --- | --- | --- | --- | --- | --- | --- | --- | --- | --- | --- | --- | --- | --- |
| ACT | GTG | GCC | TGC | AGC | ATC | TCT | GCA | CCC | GCC | CGC | TGC | CCC | AGC | CCC |
| CTT | GCA | CTT | GTC | ACA | AAC | AGT | GCA | CCT | ACT | TCA | AGT | TCT | ACA | AAG |
| AAC | GAG | GCT | TAT | GTG | CAC | GAT | GCA | CCT | GTA | CGA | TCA | CTG | AAC | TGC |
| GTG | TTG | CCT | GCT | GCC | TCC | CCT | GCC | CCA | GTA | CCC | CCA | GGA | GAA | GAT |
| CTG | GTC | CCC | CCC | GGA | CTC | CAA | GCT | CCC | ATG | ACC | CAG | ACA | ACG | CCC |
|     |     |     |     |     |     | GCT | GCC | CCA | ACC | CGA | CCC | A |
|     |     |     |     | AT GTC | GAC | CAC | GCC | C | GTA | TCC | T A |
|     |     |     |     |     |     | CA | A | T |
|     |     |     |     |     |     | G |

```
                         1 0                         30
CGC GCG GCC CCT GTC CTC CGG CCC GAG ATG AAT CCT GCG GCA GAA
                                        Met Asn Pro Ala Ala Glu
         50                         70                         90
GCC GAG TTC AAC ATC CTC CTG GCC ACC GAC TCC TAC AAG GTT ACT
Ala Glu Phe Asn Ile Leu Leu Ala Thr Asp Ser Tyr Lys Val Thr
                         110                        130
CAC TAT AAA CAA TAT CCA CCC AAC ACA AGC AAA GTT TAT TCC TAC
His Tyr Lys Gln Tyr Pro Pro Asn Thr Ser Lys Val Tyr Ser Tyr
         150                        170
TTT GAA TGC CGT GAA AAG ACA GAA AAC TCC AAA TTA AGG AAG
Phe Glu Cys Arg Glu Lys Lys Thr Glu Asn Ser Lys Leu Arg Lys
                         190                        210
GTG AAA TAT GAG GAA ACA GTA TTT TAT GGG TTG CAG TAC ATT CTT
Val Lys Tyr Glu Glu Thr Val Phe Tyr Gly Leu Gln Tyr Ile Leu
         230                        250                        270
AAT AAG TAC TTA AAA GGT AAA GTA GTA ACC AAA GAG AAA ATC CAG
Asn Lys Tyr Leu Lys Gly Lys Val Val Thr Lys Glu Lys Ile Gln
```

FIG. 2B

```
GAA GCC AAA GAT GTC TAC AAA GAA CAT TTC CAA GAT GAT GTC TTT
Glu Ala Lys Asp Val Tyr Lys Glu His Phe Gln Asp Asp Val Phe
            290                                 310

AAT GAA AAG GGA TGG AAC TAC ATT CTT GAG AAG TAT GAT GGG CAT
Asn Glu Lys Gly Trp Asn Tyr Ile Leu Glu Lys Tyr Asp Gly His
                330                     350

CTT CCA ATA GAA ATA AAA GCT GTT CCT GAG GGC TTT GTC ATT CCC
Leu Pro Ile Glu Ile Lys Ala Val Pro Glu Gly Phe Val Ile Pro
        370                     390

AGA GGA AAT GTT CTC TTC ACG GTG GAA AAC ACA GAT CCA GAG TGT
Arg Gly Asn Val Leu Phe Thr Val Glu Asn Thr Asp Pro Glu Cys
            410                     430                 450

TAC TGG CTT ACA AAT TGG ATT GAG ACT ATT CTT GTT CAG TCC TGG
Tyr Trp Leu Thr Asn Trp Ile Glu Thr Ile Leu Val Gln Ser Trp
                510                     530

TAT CCA ATC ACA GTG GCC ACA AAT TCT AGA GAG CAG AAG AAA ATA
```

FIG. 2C

```
Tyr Pro Ile Thr Val Ala Thr Asn Ser Arg Glu Gln Lys Lys Ile
                                        570
TTG GCC AAA TAT TTG TTA GAA ACT TCT GGT AAC TTA GAT GGT CTG
Leu Ala Lys Tyr Leu Leu Glu Thr Ser Gly Asn Leu Asp Gly Leu
   590                    610                           630
GAA TAC AAG TTA CAT GAT TTT GGC TAC AGA GGA GTC TCT TCC CAA
Glu Tyr Lys Leu His Asp Phe Gly Tyr Arg Gly Val Ser Ser Gln
                         650                            670
GAG ACT GCT GGC ATA GGA GCA TCT GCT CAC TTG GTT AAC TTC AaA
Glu Thr Ala Gly Ile Gly Ala Ser Ala His Leu Val Asn Phe Lys
             690                              710
GGA ACA GAT ACA GTA GCA GGA CTt GCT CTA ATT AAA TAT TAT TAT
Gly Thr Asp Thr Val Ala Gly Leu Ala Leu Ile Lys Tyr Tyr Tyr
                              750
GGA ACG AAA GAT CCT GTT CCA GGC TAT TCT GTT CCA GCA GCA GAA
Gly Thr Lys Asp Pro Val Pro Gly Tyr Ser Val Pro Ala Ala Glu
   730                      790                          810
CAC AGT ACC ATA ACA GCT TGG GGG AAA GAC CAT GAA AAA GAT GCT
His Ser Thr Ile Thr Ala Trp Gly Lys Asp His Glu Lys Asp Ala
   770
```

FIG. 2D

```
TTT GAA CAT ATT GTA ACA CAG TTT TCA TCA GTG CCT GTA TCT GTG
Phe Glu His Ile Val Thr Gln Phe Ser Ser Val Pro Val Ser Val
              830                       850

GTC AGC GAT AGC TAT GAC ATT TAT AAT GCG TGT GAG AAA ATA TGG
Val Ser Asp Ser Tyr Asp Ile Tyr Asn Ala Cys Glu Lys Ile Trp
      870                       890

GGT GAA GAT CTA AGA CAT TTA ATA GTA TCG AGA AGT ACA CAG GCA
Gly Glu Asp Leu Arg His Leu Ile Val Ser Arg Ser Thr Gln Ala
  910                       930                       990

CCA CTA ATA ATC AGA CCT GAT TCT GGA AAC CCT CTT GAC ACT GTG
Pro Leu Ile Ile Arg Pro Asp Ser Gly Asn Pro Leu Asp Thr Val
  950                       970                       1030

TTA AAG GTT TTG GAG ATT TTA GGT AAG AAG TTT CCT GTT ACT GAG
Leu Lys Val Leu Glu Ile Leu Gly Lys Lys Phe Pro Val Thr Glu
              1010                       1070

AAC TCA AAG GGT TAC AAG TTG CTG CCA CCT TAT CTT AGA GTT ATT
                                       1050
```

FIG. 2E

```
Asn Ser Lys Gly Tyr Lys Leu Leu Pro Pro Tyr Leu Arg Val Ile
        1090                1110                       1170

CAA GGG GAT GGA GTA GAT ATT AAT ACC TTA CAA GAG ATT GTA GAA
Gln Gly Asp Gly Val Asp Ile Asn Thr Leu Gln Glu Ile Val Glu
  1130                1150                1170

GGC ATG AAA CAA ATG TGG AGT ATT GAA AAT ATT GCC TTC GGt
Gly Met Lys Gln Met Trp Ser Ile Glu Asn Ile Ala Phe Gly
            1190                1210

TCT GGT GGA GGT TTG CTA CAG AAG TTG ACA AGA GAT CTC TTG AAT
Ser Gly Gly Gly Leu Leu Gln Lys Leu Thr Arg Asp Leu Leu Asn
            1230                1250

TGT TCC TTC AAG TGT AGC TAT GTT GTA ACT AAT GGC CTT GGG ATT
Cys Ser Phe Lys Cys Ser Tyr Val Val Thr Asn Gly Leu Gly Ile
  1270                            1290

AAC GTC TTC AAG GAC CCA GTT GCT GAT CCC AAC AAA AGG TCC AAA
Asn Val Phe Lys Asp Pro Val Ala Asp Pro Asn Lys Arg Ser Lys
```

FIG. 2F

```
1310                                                                1350
AAG GGC CGA TTA TCT TTA CAT AGG ACG CCA GCA GGG AAT TTT GTT
Lys Gly Arg Leu Ser Leu His Arg Thr Pro Ala Gly Asn Phe Val 1330                          1370                      1390
ACA CTG GAG GAA GGA AAA GGA GAC CTT GAG GAA TAT GGT CAG GAT
Thr Leu Glu Glu Gly Lys Gly Asp Leu Glu Glu Tyr Gly Gln Asp 1410                     1430
CTT CTC CAT ACT GTC TTC AAG AAT GGC AAG GTG ACA AAA AGC TAT
Leu Leu His Thr Val Phe Lys Asn Gly Lys Val Thr Lys Ser Tyr 1450                          1470
TCA TTT GAT GAA ATA AGA AAA AAT GCA CAG CTG AAT ATT GAA CTG
Ser Phe Asp Glu Ile Arg Lys Asn Ala Gln Leu Asn Ile Glu Leu 1490                     1510                1530
GAA GCA GCA CAT TAG CAT TAG GCT TTA TGA CTG GGT GTG TGT GTG
Glu Ala Ala His End His End

```
                                              1550.                                    1570.
TAT GTA ATA CAT AAT GTT TAT TGT ACA GAT GTG TGG GGT TTG TGT
TTT ATG ATA CAT TAC AGC CAA ATT TTT ATT TGT TGG TTT ATG GAC ATA
CTG CCC TTT CAT TTT TCT TTT CCA TCT TTT AGG TGA TCT CAA
ATT AGG AAA TGC ATT TAA CCA TGT AAA AGA TGA GTG CTA AAG TAA
GCT TTT TAG GGC CCT TTG CCA ATA GGT AGT CAT TCA ATC TGG TAT
TGA TCT TTT CAC AAA TAA CAG AAC GAA ACT TTT ATA TAT AAC
TGA TGA TCA CAT AAA ACA GAT TTG CAT AAA ATT ACC ATG ATT GCT
TTA TGT TTA TAT TTA ACT TGT ATT TTT GTA CAA ACA AGA TTG TGT
AAG ATA TAT TTG AAG TTT CAG TGA TTT AAC AGT CTT TCC AAC TTT
TCA TGA TTT TTA TGA GCA CAG CAG ACT TTC AAG AAA ATA CTT GAA AAT
AAA TTA CAT AAA GTT CTT TGT TCC ATT ATT AAT GTA CAA TTT CAT GGC
CTT AAC AAA GTT ATA GTT TGT GTT CTA TAA ACC GTA CCC CTT TAT GTC
GGG ACA TAC CCT ATA GAA CTA TAA AGA AAA TTA TGG TTC TTA GAA
TAT GTA TTA ATC ATT CTA GTA TTA TTT TAT AGG ATC TTG GTT CTG
GAA TGT CTA GGC ACT GTA GCC CAT CAG AAA TTT GAA CCT GTT CAA TTT
TTG TAC CAG AAT GGC CCC AAA GCC CAG AGG GGC AAT ATG CAC CTC GTA
TAT ATG TCA GAG TGA ATT TGT TTT TCT AAT TTT CTG CTC AAG ATT
TTA AGG AGA TAA TAA TGT TAG AGA GAA CAA TTA CAA CCA AAG CTA
AAT ATA TAC ATA AAT GTA AAA TAC TTA TGG TAG
```

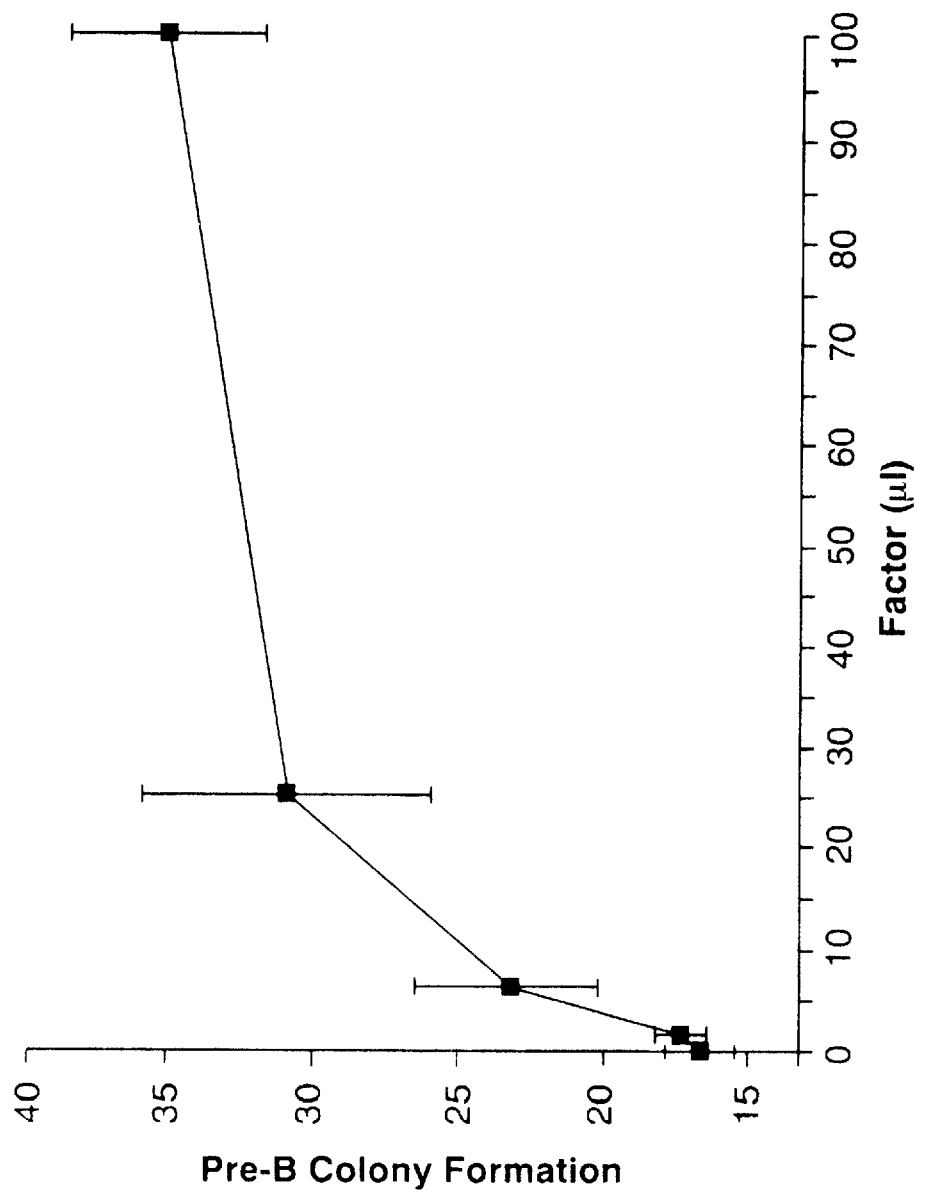

PROGENITOR B CELL STIMULATING FACTOR

This application is a divisional of U.S. Ser. No. 08/294,770, filed Aug. 23, 1994, now U.S. Pat. No. 5,580,754, which is a continuation of U.S. Ser. No. 07/980,524 filed Nov. 20, 1992, now abandoned.

The present invention relates to a novel factor, progenitor B cell stimulating factor, having the activity of promoting the proliferation and differentiation of hematopoietic progenitor cells. The invention also relates to DNA sequences encoding such factors, to polypeptide fragments and analogs thereof, and methods and compositions for the treatment of hematopoietic disorders using the factor.

BACKGROUND OF THE INVENTION

Hematopoietic growth factors are the major regulatory molecules supporting constitutive and inducible hematopoiesis (Brach et al. *Acta. Haematol.* 86, 128 (1991)). The hematopoietic growth factors (colony stimulating factors and interleukins), growth-factor synergizing factors, and growth factor-releasing factors control the proliferation, differentiation, and functional activation of hematopoietic stem cells and lineage-committed progenitor cells. Each colony stimulating factor has distinct lineages of bone marrow cells upon which they act, although there is some overlap in lineage activity and synergy between colony stimulating factors. In several instances, the involvement of growth factors in the maturation of specific hematopoietic cell types is well known, as in the action of erythropoietin to produce erythrocytes and granulocyte colony stimulating factor to produce neutrophils. However, there are a number of stages in hematopoietic cell development where the identification of stimulatory factors is incomplete or lacking altogether. This is particularly true for those events leading to the proliferation and development of early hematopoietic progenitor cells.

Hematopoietic progenitor cells develop gradually from pluripotent to unipotent, committed progenitor cells during which process they lose their self-renewal capacity (Olofsson *Aca. Oncol.* 30, 889 (1991)). This development is dependent on interactions of specific hematopoietic growth factors, which by binding to surface receptors on the stem cells stimulate them to proceed to the next step of differentiation. Interleukin-3 (IL-3) is primarily a proliferative stimulus for the undifferentiated progenitor cells (Ponting et al. *Growth Factors* 4, 165 (1991)). Granulocyte Macrophage-Colony Stimulating Factor (GM-CSF) also plays a major role in multipotent stem cell survival, proliferation and differentiation into stem cells with restricted maturation programs. The programmed unipotent stem cells need stimulation by erythropoietin, granulocyte-colony stimulating factor (G-CSF), macrophage colony stimulating factor (M-CSF) and IL-5 to proliferate and mature into their end stage products, erythrocytes, neutrophils, monocytes and eosinophils respectively. Other cytokines such as IL-1β, IL-4 and IL-6 fulfill important functions as cofactors in these processes (Arai et al. *Ann. Rev. Biochem.* 59, 783 (1990)).

Stem cell factor (SCF), also referred to as the ligand for c-kit, was recently identified as a cytokine which stimulates the proliferation of progenitor cells (PCT Application No. WO 91/05795). SCF has the capacity to synergize with a wide variety of other hematopoietic growth factors to cause the proliferation and differentiation of committed progenitor cells (Migliaccio et al. *J. Cell Physiol.* 148, 503 (1991)). In clonal cultures of normal mouse marrow cells, combination of G-CSF, GM-CSF or IL-3 with SCF induced up to 25 fold increase in the mean cell content and up to 6-fold increase in their mean progenitor cell content (Metcalf *Proc. Natl. Acad. Sci. USA* 88, 11310 (1991)).

Progenitor cells committed to the lymphoid lineage eventually mature to B or T lymphocytes. Mature B cells mediate humoral antibody responses by producing antibodies which circulate in the bloodstream and bind foreign antigens. The binding of antigen by antibody leads to antigen destruction by phagocytosis or by activation of complement. Antibody-producing B cells comprise a major part of the human immune response.

The involvement of growth factors in the proliferation and differentiation of hematopoietic progenitor cells to mature B cells is essential for maintaining B cell levels. The identification of such factors will be important in developing therapeutic strategies for modulating B cell levels, particularly in immunodeficient patients. One area of research is the identification of factors acting early in B cell development to stimulate the production of B cell progenitors such as pre-B cells. Pre-B cells are characterized as the early progenitor cells which express the μ heavy chain of immunoglobulin in their cytoplasm but do not express cytoplasmic light chain or surface immunoglobulin.

U.S. Pat. No. 4,965,195 disclosed that interleukin-7 (IL-7) stimulates the proliferation of pre-B cells derived from mouse bone marrow. McNiece et al. (*J. Immunol.* 146, 3785 (1991)) showed that SCF interacts synergistically with IL-7 to stimulate proliferation of B lineage cells. However, the requirement for additional factors in B cell formation has been suggested by the work of Billips et al. (*Blood* 79, 1185 (1992)). The Billips et al. reference demonstrates that pre-B cell formation from B220-, Ig-progenitor cells and expression of μ heavy chain of immunoglobulin is uniquely dependent on the presence of S17 stromal cells and can not be reproduced with IL-7, SCF, or costimulation with both IL-7 and SCF. In addition, stromal derived lymphopoietic factor-1 (SDLF-1) that alone stimulates the differentiation of B progenitor cells into pre-B cells has been described (PCT Application No. WO 89/06541).

It is therefore an object of the invention to identify factors that are involved in promoting the proliferation and differentiation of hematopoietic progenitor cells, particularly lymphoid progenitor cells, into B lineage committed cells such as pre-B cells. The factors of the invention are useful as modulators of the humoral antibody response. The therapeutic benefit of factors acting to stimulate B cell progenitors makes it desirable to identify and express the genes encoding said factors.

SUMMARY OF THE INVENTION

The present invention provides for a novel factor having the ability to stimulate the proliferation and differentiation of hematopoietic progenitor cells, specifically progenitor B cells. The factor is referred to herein as progenitor B cell stimulating factor, or PBSF. PBSF may have the amino acid sequence as set forth in SEQ ID NO. 1 SEQ ID NO. 2. The invention also includes allelic variants, fragments and analogs of PBSF having the activity of stimulating the proliferation and differentiation of progenitor B cells. PBSF may be purified from natural sources, e.g., mammalian tissues or cell lines, or may be the product of procaryotic or eucaryotic expression of an exogenous DNA sequence, i.e., derived by recombinant means.

DNA sequences encoding biologically active PBSF are included in the present invention. Such DNA sequences include the sequence set forth in SEQ ID NO. 1 as well as allelic variants, fragments and analogs having biological activity. Also provided are vectors containing such DNA sequences and host cells transformed or transfected by such vectors. The production of the factor by the steps of growing, under suitable nutrient conditions, transformed or transfected host cells in a manner to allow expression of the polypeptide and isolating the factor is also contemplated.

PBSF is shown to stimulate the proliferation and differentiation of hematopoietic progenitor cells committed to the lymphoid lineage, such as B cell progenitors, in the presence of stem cell factor and interleukin-7.

The invention also relates to antibodies specifically binding PBSF, binding to a fusion polypeptide comprising PBSF, or to a peptide fragment containing a portion of the amino acid sequence of PBSF.

Pharmaceutical compositions comprising the factor and methods of treating hematopoietic disorders using the factor are also provided.

BRIEF DESCRIPTION OF THE FIGURES

FIG. 1 shows the nucleotide sequences encoding the signal peptidase cleavage sites of GM-CSF SEQ ID NO. 3, SEQ ID NO. 5 IL-1 β, SEQ ID NO. 4 IL-2, SEQ ID NO. 7 IL-3 and SEQ ID NO. 6 IL-6. Also shown is the sequence of the degenerate oligonucleotide probe SEQ ID NO. 8 that was designed based upon the signal peptidase cleavage sites and used in screening libraries for cytokines.

FIG. 2A–G shows the nucleotide and deduced amino acid sequence of PBSF SEQ ID NO. 1 and SEQ ID NO. 2.

FIGS. 5A–C show the activity of PBSF in a pre-B cell colony formation assay. PBSF is derived from conditioned medium from transfected COS cells (A), conditioned medium from transfected PA317 cells (B) or from affinity purification of conditioned medium from transfected PA317 cells (C).

DETAILED DESCRIPTION OF THE INVENTION

Figure 3:
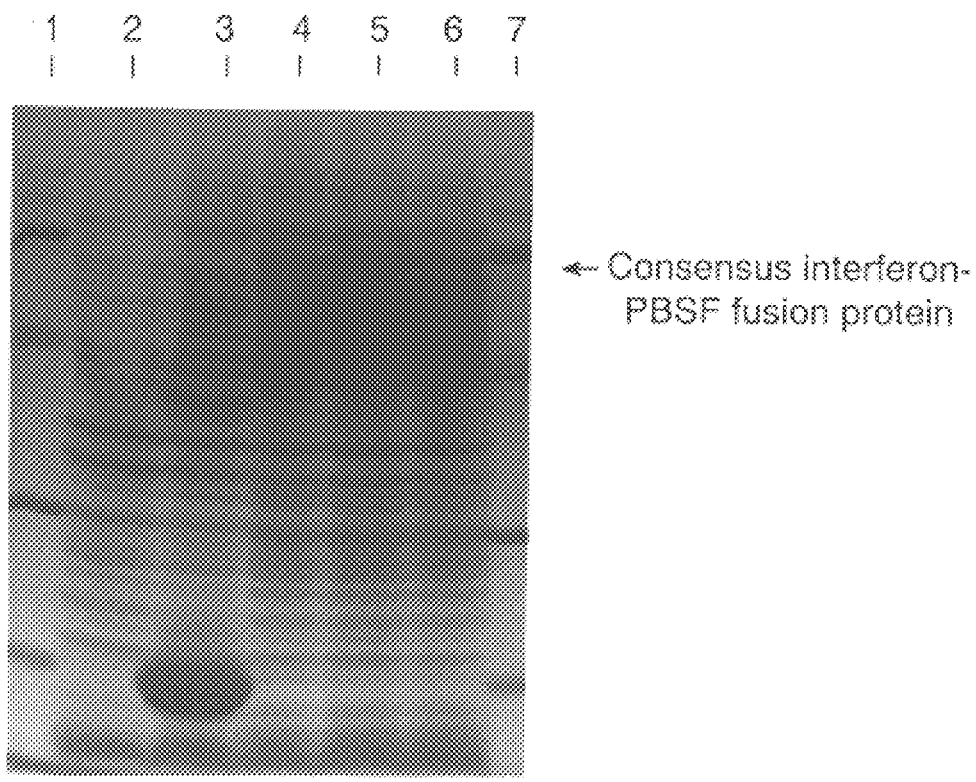
FIG. 3 shows the expression of the consensus interferon-PBSF fusion protein in E. coli. Lane 1, molecular weight markers; Lane 2, consensus interferon-PBSF fusion gene inserted in wrong orientation; Lane 3, consensus interferon gene; Lanes 4, 5 and 6, consensus interferon-PBSF fusion gene in correct orientation; Lane 7, molecular weight markers
Figure 4:
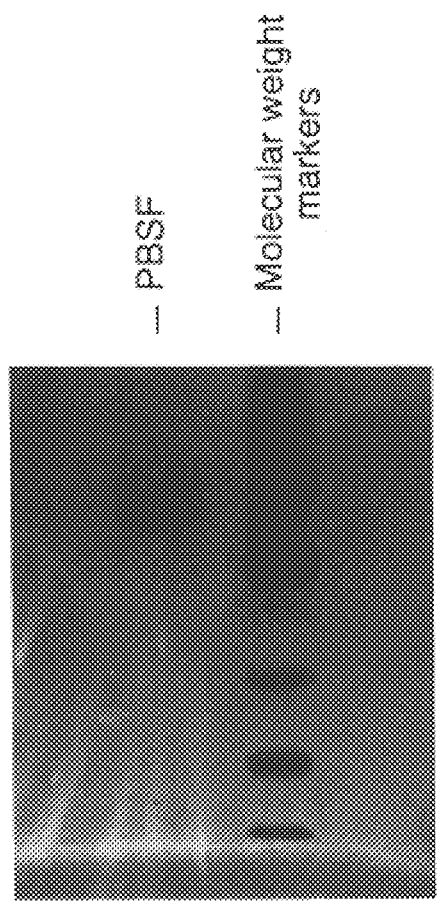
FIG. 4 shows SDS-PAGE of PBSF expressed in PA317 cells and affinity purified by immobilized anti-PBSF antibody.

The present invention provides for a novel factor which is a polypeptide having the ability to stimulate the proliferation and differentiation of hematopoietic progenitor cells committed to lymphoid lineage. The factor is referred to as progenitor B cell stimulating factor, or PBSF. The term progenitor B cell" is taken to mean a cell which has the capacity to give rise to mature B lymphocytes. In one embodiment, PBSF, in conjunction with IL-7 and SCF, is shown to stimulate the proliferation and differentiation of lymphoid progenitor cells to pre-B cells.

The biological activity of PBSF was determined by in vitro and in vivo assays described in Examples 5 and 6. Example 5 discloses an in vitro colony forming assay in which the number and types of colonies from 5-fluorouracil treated mouse bone marrow arising after exposure to PBSF and other growth factors is described. Example 4 discloses in vivo assays for PBSF activity involving the introduction and expression of the PBSF gene in transgenic mice, retroviral infection of baby mice with the PBSF gene and introduction and expression of the PBSF gene by mouse bone marrow transplantation.

The results from in vitro experiments (Example 5) show that PBSF stimulates the formation of B progenitor cells from mouse bone marrow cultures in the presence of SCF and IL-7. As disclosed in the specification, PBSF appears to act synergistically with SCF and IL-7 to promote the proliferation and differentiation of lymphoid progenitor cells to pre-B cells. As shown in FIG. 5, there is no stimulation of pre-B cell colony formation when either the combination of SCF and IL-7 alone or PBSF alone is added to mouse bone marrow cells. There is, however, a 50% increase in the number of pre-B cells when SCF, IL-7 and PBSF are added together to bone marrow cells in culture.

The factor of the present invention is a polypeptide that may be isolated from natural sources, e.g., mammalian tissues or cell lines which are known to be a source of cytokines or growth factors. PBSF was shown to be expressed in peripheral blood lymphocytes induced with PWM and in the human cell line Hut 78 induced with PMA (see Example 1). Alternatively, the factor may be isolated as a product of procaryotic or eucaryotic expression of an exogenous DNA sequence, i.e., derived by recombinant means.

In one embodiment, PBSF has the amino acid sequence as set out in FIG. 2A–G and SEQ ID NO. 1SEQ ID NO. 2. The amino acid sequence may be of the mature polypeptide or it may be of the unprocessed polypeptide. Processing of the factor to a mature protein will involve cleavage of a leader sequence, which is predicted to occur between amino acid residues 14 and 15 as shown in SEQ ID NO. 1, such that mature PBSF will have an amino terminal residue at $Thr^{15}$. Alternatively, cleavage of the leader sequence may occur between amino acid residues 31 and 32 as shown in SEQ. ID. NO. 1 SEQ ID NO. 2 such that mature PBSF will have amino terminal residue at $Lys^{32}$. Other processing events could also occur, such as cleavage of one or more amino acids from either the mature amino terminus or carboxy terminus of the predicted polypeptide. Some of these processing events may convert the polypeptide to a biologically active form.

Biologically active PBSF variants are also provided. The variants include naturally occurring allelic variants, substitution analogs wherein one or more amino acids have been substituted with different amino acids, deletion analogs wherein one or more amino acids have been deleted and addition analogs wherein one or more amino acids have been added. Deletions and additions of one or more amino acids are made either within an internal region of the polypeptide or at the amino or carboxyl terminal ends. Polypeptides of the invention may also include an initial methionine residue at the amino terminal end.

Polypeptides of the invention fused to heterologous polypeptides are also provided for. In a preferred embodiment, the mature amino acid sequence of PBSF is fused at the carboxyl terminus to human alpha interferon or bovine growth hormone. The resulting fusion protein is expressed at high levels in *E. coli* host cells. Such fusion polypeptides are useful for the production of antibodies which specifically bind PBSF as described in Example 3. In addition, peptide fragments which are chemically synthesized may also be used to produce antibodies that bind specifically to the factor.

The present invention also provides for novel DNA sequences encoding biologically active PBSF. Preferably, the sequences comprise:

a) the DNA sequences as set out in SEQ ID NO. 1 and its complementary strand;

b) DNA sequences hybridizing to the sequences in (a); and c) DNA sequences which, but for the degeneracy of the genetic code, would hybridize to the sequences in (a) and (b).

DNA sequences of the invention include those sequences coding for the mature, processed form of the polypeptide as well as for precursor forms of the polypeptide. DNA sequences coding for precursor forms of the polypeptide contain, for example, leader sequences necessary for secretion.

cDNA sequences encoding part or all of the coding region of PBSF were obtained as described in Example 1. An oligo (dT) primed cDNA library prepared from peripheral blood lymphocytes was screened by hybridization to a set of mixed oligonucleotide probes having the sequences as shown in SEQ. ID. NO. 8. The screening procedure is described in Example 1G. The probes were designed on the basis of an observed nucleotide sequence homology around the signal peptidase cleavage sites encoded by GM-CSF (SEQ ID. NO. 3), IL-1β (SEQ. ID. NO. 5), IL-2 (SEQ. ID. NO. 4), IL-3 (SEQ ID. NO. 7) and IL-6 (SEQ. ID. NO. 6) mRNAs. The rationale for this screening approach was to identify other cytokines using probes specific for the secreted portion of cytokine-like molecules. One cDNA clone which hybridized was originally designated P64 but lacked the entire coding region. Subsequently, the entire coding region of P64 was obtained on a 1.78 kb cDNA clone from a random primed peripheral blood lymphocyte cDNA library. The clone was found to have activity in stimulating pre-B cell formation and the expressed protein was referred to as PBSF. This 1.78 kb. fragment encoding PBSF was inserted into the plasmid V19.12 and transformed into *E. coli* strain DH5 alpha F' for deposit with the American Type Culture Collection (ATCC) under accession no. 69133 on Nov. 25, 1992. Because of the high degeneracy of the probe mixture (about 65,000 fold), positively hybridizing clones were obtained which had sequences similar to the signal peptidase cleavage site in other regions of the molecule. This was the case with the gene encoding PBSF.

DNA sequences of the invention may be cDNA and genomic DNA sequences isolated from human and other mammalian sources. Also contemplated are synthetic DNA sequences encoding PBSF, and fragments thereof, which are readily produced by gene synthesis techniques well known in the art. DNA sequences encoding PBSF disclosed in the present application, and fragments thereof, may be used as probes to isolate genomic DNA encoding PBSF. In addition, DNA sequences containing part or all of the PBSF gene are useful in detecting the presence of the gene in biological samples, in mapping the position of the gene on the human chromosome, and in nucleic acid-based therapeutics, such as anti-sense or triple helix blocking, where it is desirable to regulate the quantities of PBSF that are synthesized.

The DNA sequences also include sequences coding for biologically active PBSF variants. The sequences include those coding for naturally occurring allelic variants, substitution analogs, deletion analogs and addition analogs, wherein the deletions and additions may be introduced at the amino or carboxyl terminus or within the coding region. Techniques that are well known in the art are employed to construct such analogs. Such variants may have a number of desirable properties, e.g., more resistant to proteolysis, more resistant to oxidation, or more easily refolded upon expression in microbial hosts, while still retaining biological activity.

DNA sequences include those coding for fusion proteins, wherein part or all of the DNA sequence of PBSF is fused to a heterologous protein. Preferably, DNA sequences coding for part of human consensus interferon or bovine growth hormone are fused in frame to the 5' end of the DNA sequence encoding PBSF. The construction of fusion proteins is described in Example 3A. As shown in Example 3B, such fusion proteins are useful for the production of antibodies to the factor.

PBSF is characterized by being the product of procaryotic or eucaryotic host expression (e.g., by bacterial, yeast, plant, insect and mammalian cells in culture) of exogenous DNA sequences, wherein the exogenous DNA sequences may be cDNA, genomic DNA or synthetic DNA. That is, in a preferred embodiment, the factor is derived by recombinant means. As hematopoietic growth factors are generally produced in only small quantities by natural sources, the ability to produce the factor by recombinant methods is essential to obtaining quantities sufficient for therapeutic applications.

A variety of vectors are readily available for the expression of DNA sequences encoding PBSF in host cells. Vectors such as V19.12, pDSRα2 and mpZen have been described in Examples 2A–C for the expression of PBSF in COS, Chinese Hamster Ovary (CHO) and PA317 mammalian cell lines, respectively. In addition, PBSF may be expressed in a number of vectors suitable for use in yeast and bacterial strains. As described in Example 2, PBSF was expressed as a fusion protein with either human alpha interferon or bovine growth hormone sequences in *E. coli* using the vector pCFM 756. PBSF sequences may be optimized for expression in a particular host system, whether it be a bacterial, yeast, or mammalian host cell. Such optimization may involve the inclusion of preferred codons for expression. In one preferred embodiment, the PBSF sequences include one or more codons optimized for expression in *E. coli* host cells. Also provided for are vectors for the expression of PBSF in transgenic mice as described in Example 4A.

A process for the production of recombinant PBSF is also described. The process comprises growing, under suitable nutrient conditions, procaryotic or eucaryotic host cells transformed or transfected with a DNA sequence encoding biologically active PBSF and isolating PBSF expressed by said DNA sequence. Preferably, the sequence is that set forth in SEQ ID NO. 1 and sequences hybridizing thereto.

Depending upon the host cell used for expression, the polypeptide of the invention may be glycosylated or nonglycosylated. Mammalian proteins are usually modified by the attachment of carbohydrate chains at specific locations along the amino acid backbone. Attachment of carbohydrate chains at selected asparagine residues is termed N-glycosylation while carbohydrate at serine or threonine residues is termed O-glycosylation. The presence of either N-linked or O-linked chains, or both, may be required for biological activity and/or stability of the polypeptide. The existence of N-linked glycosylation sites can be predicted by the sequence Asn-X-Ser/Thr where X can be any amino acid. Based upon this, PBSF is predicted to have two N-linked glycosylation sites at $Asn^{29}$ and $Asn^{396}$.

The PBSF polypeptide may also be modified with a water soluble polymer such as polyethylene glycol. Covalent attachment of water soluble polymers to proteins is carried out using techniques known to those skilled in the art and have been described in U.S. Pat. No. 4,179,937, hereby incorporated by reference. The modified polypeptide may have desirable properties such as increased solubility in aqueous solutions, increased stability, longer in vivo half-life and increased biological activity.

PBSF may also be covalently attached to a detectable label which may be radioactive (e.g., $I^{125}$) or nonradioactive (e.g., a fluorescent dye). The attachment of a reporter group provides reagents useful for the detection of PBSF in solid tissues and fluid samples. Similarly, DNA sequences encoding PBSF may be covalently attached to detectable labels for use as probes for PBSF sequences in biological samples, for example, in mapping the location of the human PBSF gene in the genome and for detecting the presence of PBSF related sequences.

Antibodies specifically binding the factor are also comprehended by the invention. The antibodies may be monoclonal or polyclonal and may bind specifically to polypeptide fragments and fusion polypeptides as well as to the intact protein. The production of antibodies to a human consensus interferon-PBSF fusion protein and a bovine growth hormone-PBSF fusion protein is described in Example 3B. Antibodies are useful in quantitating the amount of factor in biological samples (e.g., blood or urine). Abnormal concentrations of the factor may be a useful indicator of certain hematopoietic disorders. Further, antibodies specifically binding PBSF are useful in a method for the purification of the polypeptide, either from natural sources or from expression of recombinant plasmids, wherein the method comprises the steps of:

a) attaching an antibody to a solid support, b) contacting said attached antibody with a solution containing the polypeptide in such a manner as to selectively bind the polypeptide to the antibody; and c) eluting the bound polypeptide.

The solution containing the polypeptide may be a crude or partially purified mixture. The purification of PBSF using an anti-PBSF antibody affinity column is described in Example 5.

The invention provides for pharmaceutical compositions comprising therapeutically effective amounts of PBSF together with pharmaceutically acceptable diluents, adjuvants, carriers, preservatives, emulsifiers and/or solubilizers. A "therapeutically effective amount" as used herein refers to that amount which provides therapeutic effect for a given condition and administration regiment. It is expected that one skilled in the art would be able to determine a therapeutically effective amount of PBSF for any given condition being treated. Pharmaceutical compositions include diluents of various buffers (e.g., Tris, acetate, phosphate), solubilizers (e.g., Tween, Polysorbate), carriers such as human serum albumin, preservatives (thimerosal, benzyl alcohol) and anti-oxidants such as ascorbic acid. The factor may also be incorporated into particulate preparations of polymeric compounds for controlled delivery to a patient over an extended period of time. A more extensive survey of components in pharmaceutical compositions is found in Remington's *Pharmaceutical Sciences,* 18th ed. A. R. Gennaro, ed., Mack, Easton, Pa. (1990).

Dosage of PBSF used to treat hematopoietic disorders will vary depending upon a number of factors, including the nature and severity of the disorder being treated, the route of administration, the use of PBSF in combination with other therapy. Also to be considered is the in vivo half-life of the PBSF polypeptide or a modified form thereof wherein the modification can be with a water soluble polymer such as polyethylene glycol. A "therapeutically effective amount" of PBSF as used herein can be determined by one skilled in the art taking into account these factors.

PBSF may be administered by injection, either subcutaneous, intravenous or intramuscular, or by oral or nasal administration. The route of administration will depend upon the particular condition being treated.

PBSF is used alone or in combination with other therapy in the treatment of a number of hematopoietic disorders. In a preferred embodiment, PBSF is used in combination with SCF and IL-7 for the treatment of B cell disorders. The factor may also be used with other factors known to be involved in various stages of hematopoiesis such as IL-1, IL-2, IL-3, IL-4, IL-5, IL-6, low molecular weight B cell growth factor (L-BCGF), or high molecular weight B cell growth factor (H-BCGF) for the treatment of B cell disorders. Administration of other hematopoietic factors may be concurrent with, prior to, or after administration of PBSF.

PBSF may be used alone or in conjunction with other factors to treat a number of hematopoietic disorders that result from disease or injury to bone marrow. These disorders include the following: cytopenia, aplastic anemia, myelodysplastic syndrome, leukemic disease, and stem cell transplantation. In addition, marrow injury resulting from radiation treatments or chemotherapy leads to myelosuppression which may be overcome by treatments with the factor. In a preferred embodiment, PBSF is administered in conjunction with SCF and IL-7 for the treatment of B cell disorders, particularly those disorders involving decreased levels of B cells. A deficiency in B lymphocytes leads to a depressed immune response and a greater susceptibility to disease. PBSF is advantageously administered to an immunocompromised patient.

PBSF will be useful in expanding B progenitor, cells in bone marrow prior to syngeneic, allogeneic or autologous bone marrow transplantation. The factor may be administered directly to patients to increase the production of B progenitor cells in the marrow or administered ex vivo to marrow cultures prior to transplantation. It is expected that such treatment will reduce the period of depressed immunity experienced by patients after transplantation.

The following examples are offered to more fully illustrate the invention, but are not to be construed as limiting the scope thereof.

EXAMPLE 1

Identification of a cDNA Clone (P64) Encoding PBSF

A. Isolation of lymphocytes

Peripheral blood lymphocytes were isolated from freshly prepared buffy coats obtained from Hemacare (Sherman Oaks, Calif.). Buffy coats were diluted three times with phosphate buffered saline (PBS). 30 ml of the diluted buffy coats were pipetted into 50 ml culture tubes (Fisher Scientific, Pittsburgh, Pa.) and underlaid with 10 ml of Ficoll-Paque (Pharmacia, Piscataway, N.J.). After centrifugation at 3200×g, the mononuclear cells present in the interphase were removed and washed three times in 30 ml each of PBS. The pellet was then suspended in 50 ml of RPMI 1640 and 10% fetal bovine serum (FBS), diluted 50 fold and cell number determined.

B. Induction of Cytokine Expression

About $5 \times 10^6$ cells/ml were incubated with poke weed mitogen (PWM; 10 μg/ml. Sigma, St. Louis, Mo.) for 19 hours followed by addition of cycloheximide (Sigma) to 10 μg/ml for an additional 6 hours. For comparison, the same amount of cells were incubated with or without PWM for the same time period. Incubation was carried out at 37° C. and 5% $CO_2$.

C. Isolation of RNA

Total RNA from induced peripheral blood lymphocytes was isolated using the guanidinium thiocyanate technique (Chirgwin et al. *Biochemistry*, 18, 5294 (1979)). Briefly, cells were collected by centrifugation and lysed in a solution of 4M guanidinium thiocyanate containing 4% mercaptoethanol. Adherent cells were lysed in the same solution and pooled. After three passages through an 18 gauge needle, the lysate was overlaid on a step gradient of 5.7M cesium chloride. Centrifugation at 76,000×g was carried out in a Beckman L2 ultra centrifuge for 24 hours at 20° C. After centrifugation, pelleted RNA was suspended in 10 mM Tris, 1 mM EDTA, pH 7.5 plus 0.1% SDS and precipitated by the addition of 2.5 volumes of 100% ethanol and sodium acetate (pH 5.0) to 0.3M.

D. Selection of poly(A)+ RNA poly(A)$^+$ RNA was selected by chromatography on oligo (dT)-cellulose (Collaborative Research, Bedford, Mass.) using procedures described in Maniatis et al. (*Molecular Cloning, A Laboratory Manual*, 1st ed. Cold Spring Harbor Laboratory, Cold Spring Harbor, N.Y. (1982)), ethanol precipitated, and centrifuged. The final pellet was dissolved in distilled water and stored in liquid nitrogen in aliquots.

E. cDNA library construction

About 5 μg of polyA+ RNA in 10 μl was denatured with 10 mM methyl mercury hydroxide at room temperature for 10 min, followed by the addition of P-mercaptoethanol to 10 mM and RNasin (Promega, Madison, Wis.) to 3 u/μl and incubation at room temperature for 5 min. The following components were then added to the indicated final concentrations: 50 μg/ml oligo(dT), 2 mM dNTP (Pharmacia), 100 μg/ml. bovine serum albumin, first strand buffer (50 mM Tris-HCl, pH 8.6, 75 mM KCl, 10 mM $MgCl_2$, Bethesda Research Laboratories, Gaithersburg, Md.) and 20 u/μl Superscript reverse transcriptase (BRL). First strand synthesis was allowed to proceed at 37° C. for one hour. The mixture was then diluted with the second strand buffer (20 mM Tris-HCl, pH 7.5, 5 mM $MgCl_2$, 100 mM KCl, 50 μg/ml. bovine serum albumin, 10 mM dithiothreitol, BRL), 0.125 u/μl. *E. coli* DNA polymerase I (BRL), 0.08 u/μl Rnase H (BRL), 0.1 u/μl *E. coli* DNA ligase (New England Biolabs, Beverly, Mass.) and 0. 15 mM NADP (Sigma). All concentrations stated are those in the reaction mixture. The mixture was incubated at 15° C. for 1 hour followed by one hour at 25° C. T4 DNA polymerase (Pharmacia) was then added to 0.01 u/μl and the reaction incubated at 37° C. for 30 min. to generate blunt ends. Unincorporated dNTPs were removed by two ethanol precipitations in the presence of 2M ammonium acetate.

The double-stranded cDNA was then methylated with Eco RI and Alu I methylases (Boehringer Mannheim, Indianapolis, Ind.) according to the following procedure. To double-stranded cDNA in water was added methylation buffer, 100 uM S-adenosyl methionine, and 1 u/μl of Alu I methylase and incubated at 37° C. for one hour. Then NaCl was added to 0.1M and EcoRI methylase added to 10 u/μl. The reaction was incubated at 37° C. for 30 min.

The oligo-adaptor having the sequence 5' GCT TGA ATT CAA GC 3' (see SEQ ID. NO. 9) was ligated to the cDNA overnight. cDNA was electrophoresed on a 0.8% agarose gel and molecules longer than 500 bps. were electro-eluted from the gel. The eluted cDNA was extracted with a 1:1 mixture of phenol/chloroform, precipitated with ethanol, suspended in water and digested sequentially with Hind III and Eco RI restriction enzymes to generate Eco RI cohesive ends on the 5' end of the molecules and Hind III cohesive ends on the 3' end of the molecules.

A 592 bp. Aat II/Cla I fragment containing the origin of replication from bacteriophage M13 was inserted into the eucaryotic expression V19.8, which was described in PCT Application No. WO 91/05795, to generate the vector V19.10. V19.10 was digested with Eco RI and Hind III and treated with bacterial alkaline phosphatase. Ligation reactions were set up at different ratios of cDNA to vector DNA and the ratio giving rise to the highest number of clones after transfection was chosen for large scale ligation. Competent DH5 αF' *E. coli* cells (Gibco-BRL) were used for transfection. The library was plated on 15 150 mm plates which were then scraped in the presence of SOB (Okayama et al. *Methods in Enzymol.* 154, 3 (1987)) and stored in 7% DMSO at –80° C.

An additional cDNA library was constructed from polyA selected RNA isolated from peripheral blood lymphocytes in which a random hexamer primer (Pharmacia) was used to prime the first strand cDNA synthesis. Double stranded flush-ended cDNA was generated as described above for the oligo dT primed library. An adaptor (In Vitrogen, San Diego, Calif., catalog no. N408-8) having the sequence as in SEQ. ID NO. 10 and SEQ ID NO. 11.

5' CTTTCCAGACACA 3' GAAAGGTC was ligated to the cDNA. V19.12 was constructed by inserting the Hind III/NotI stuffer fragment of pCDM8 (In Vitrogen) between the Hind III and Not I sites of V19.10. V19.12 was digested with Bst XI restriction enzyme and then ligated to the cDNA. Transformation of *E. coli* DH5 αF' host cells and storage of the cells was performed as described above.

F. Probe Design

Mixed oligonucleotide probes were designed on the basis of some sequence homology around the signal peptidase cleavage site of a few cytokines. The probes were designed as shown in FIG. 1 using the published sequences from GM-CSF, IL-1, IL-2, IL-3 and IL-6 encoding signal peptidase cleavage sites (Wong et al. *Science* 228, 810 (1985); Nishida et al. *Biochem. Biophys, Res. Comm.* 143, 345 (1987); Taniguchi et al. *Nature* 302, 305 (1983); Yang et al. *Cell* 47, 370 (1986); and May et al. *Proc. Natl. Acad. Sci.* 83, 8957 (1986)). The degeneracy of the probe mixture was 65,536. Due to the high degeneracy, it was possible to isolate clones which have similar sequences in regions other than the signal peptidase cleavage site.

G. Screening of cDNA Libraries

High density screening of the oligo(dT) primed peripheral blood lymphocyte library in DH5α F' *E. coli* was carried out by plating about 10,000 colonies per 150 mm plate on a GENE SCREEN PLUS membrane (New England Nuclear/DuPont, Boston, Mass.). A replica onto a second gene screen membrane was made and the colonies on the replica plate were allowed to grow overnight on an LB plate containing the drug 100 μg/ml ampicillin. The replica membranes were then placed on an LB plate containing 100 μg/ml chloramphenicol for amplification of plasmid DNA. After overnight amplification, DNA in the colonies were denatured in 0.5N NaOH and 1.5M NaCl for 5 minutes, followed by renaturation in 1M Tris-HCl pH 7.5. The membranes were air dried and baked for 2 hours at 80C. in vacuum. Filters were wet in 2× SSC, followed by two 30 min. prewashes in 6×SSC, 0.2% SDS. Prehybridization was carried out in 6×SSC, 5×Denhardt, 0.1% SDS for 4–5 hours. 20 pmoles of mixed oligonucleotide probe was labelled with $\gamma P^{32}$-ATP using T4 polynucleotide kinase and the unincorporated label was removed by centrifugation through a Sephadex G-50 column. About $2 \times 10^6$ cpm per ml was used in hybridization at 55° C. in 6×SSC, 0.1% SDS and 5×Denhardt's solution. After 20 hours the filters were washed 30 minutes twice at 55° C. in 6×SSC and 0.1% SDS. An additional wash was carried out at the same temperature in 2×SSC plus 0.1% SDS. After overnight exposure, the areas in the master plate corresponding to the positive signal area were scraped and suspended in SOB. Serial dilution of the colonies were plated on ampicillin plates for secondary screening. Individual colonies were identified and grown up overnight for isolation of plasmid DNA. A final screening was carried out by hybridizing the oligonucleotide probe to plasmid DNA from different colonies. About 80 positive clones were identified in this manner.

Plasmid DNA from positive clones were sequenced on both strands using primers hybridizing to sequences in the 19.10 vector that are 5' and 3' to the cDNA inserts. DNA sequencing of cDNA clones was carried out as described in Sanger et al. *Proc. Natl. Acad. Sci.* 74, 5463 (1977). The DNA sequence were compared to those present in various versions of the GenBank sequence database. Only those sequences not appearing in GenBank were further characterized by obtaining sequences of the full length clones and analyzing the sequences using the Genetics Computer Group (University of Wisconsin) software package. One of the clones that was pursued further was designated P64.

The P64 clone isolated from the oligo dT primed peripheral blood lymphocyte cDNA library lacked the 5' end of the gene as indicated by an absence of the initiator methionine residue. In order to obtain a full-length clone of P64, a PMA activated Hut78 λ gt11 cDNA library from Clontech Laboratories (Palo Alto, Calif., Catalog No. HL 1068b) was probed with the P64 cDNA clone. About 10,000–20,000 plaques per 150 mm plate were replica plated onto Gene Screen filters and probed with the P64 clone labelled with $^{32}P$ by the random priming method. After secondary screening, individual positive colonies were identified. The insert was released by digestion of the positive lambda cDNA clones with Eco RI and subcloned into the Bluescript SK II plasmid (Stratagene, La Jolla, Calif.) and sequenced. This clone contained upstream coding sequences, but the initiator methionine codon was still lacking.

In another attempt to obtain a full-length P64 clone, a random primed peripheral blood lymphocyte cDNA library in V19.12 was screened using the P64 cDNA clone isolated from the Hut78 library as a probe. Multiple positively hybridizing clones were obtained and the DNA inserts were subcloned into M13 mp21 and sequenced. Several clones had coding regions identical to the Hut 78 clone and in addition contained sequence coding for the initiator methionine residue. One isolate contained an insert of approximately 1780 bps. having the entire coding region of P64. This clone encodes the polypeptide designated as progenitor B cell stimulating factor or PBSF.

This 1.78 kb DNA fragment inserted into the plasmid V19.12 and transformed into *E. Coli* strain DH5α F' has been deposited with the American Type Culture Collection (ATCC) under accession number 69133 on Nov. 25, 1992.

H. DNA Sequencing and Analysis

GenBank, EMBL and Swiss Prot databases were searched to find sequences identical to or highly homologous with PBSF sequences at the nucleic acid and amino acid levels. The search was carried out using FastA and TfastA programs of the GCG Software Package. Analysis of the nucleic acid structure was carried out using Map and Translate programs. The amino acid sequence of PBSF was analyzed by the use of Pepplot, Pepstructure, Motifs and Isoelectric programs. Sigseq1 program was used to predict the signal peptide cleavage site. Multiple searches of the GenBank EMBL database were performed to compare the PBSF sequence with those present in the database. None of the searches revealed a high degree of homology between PBSF and sequences in the database.

I. The PBSF Gene and the Encoded Protein

The DNA sequence of P64 as deduced from cDNA clones obtained from the hut 78 library and from the oligo dT primed and random primed PBL libraries is shown in FIG. 2A–G and SEQ. ID. NO. 1. The sequence extends for 2376 bps. The size of the P64 protein deduced from the DNA sequence is about 52 kDa, comprising of 491 amino acids including the leader sequence. The signal peptide cleavage site is predicted to be between amino acid residues alanine at position 14 and threonine at position 15 in SEQ. ID. NO. 1 SEQ ID NO. 2 as described in von Heinje (*Nuc. Acid Res.* 14, 4683 (1986)). There is also a probability of cleavage between serine at position 31 and lysine at position 32. There is a long 3' untranslated region, containing multiple TATT and TTTT motifs, which are present in a number of cytokine molecules (Shaw et al. *Cell* 49, 659 (1986)). The predicted protein has a hydrophobic amino terminus. There are six cysteine residues. The isoelectric point is 7.25 as predicted by the program ISOELECTRIC in the GCG software package. There are two potential N-linked glycosylation sites at $Asn^{29}$ and $Asn^{396}$. In addition, there are four potential protein kinase C phosphorylation sites and five creatine kinase II phosphorylation sites.

EXAMPLE 2

Expression of Recombinant PBSF Protein

A. Expression in Cos cells

Cos cells were transfected with V19.12 DNA containing the 1.78 kb PBSF cDNA insert by electroporation. About $3 \times 10^6$ cells in PBS were electroporated using the electro cell manipulator 600 (BTX, San Diego, Calif.) at 500 volts/capacitance and resistance, capacitance at 1000 μF, resistance of 48 ohms at a charging voltage of 150 volts in a volume of 400 μl using a cuvette of 2 mm gap. The pulse length was from 8.3 to 10.5 msec. The cuvette was kept on ice for five min. followed by dilution in DMEM containing 10% fetal bovine serum and plating in a 10 cm. plate. After overnight incubation at 37° C., 5% $CO_2$, media was changed to eliminate dead cells. Serum-free DMEM was added to the plate and conditioned medium (CM) was harvested after 72 hours for bioassays. The CM was filter sterilized and frozen in aliquots at −20° C. The presence of P64 protein in the medium was detected by Western blot analysis using antibodies generated against a P64 fusion protein as described below.

B. Expression in Chinese hamster ovary (CHO) cells

CHO cells constitutively producing PBSF were generated as follows. CHO (DHFR⁻) cells were transfected with the vector pDSRα2 (PCT Application No. WO 91/05795) containing the PBSF coding region. The following primers were used in PCR to amplify the PBSF coding region:

5' TGTCCTCCGGCCCGAGATGA (Nucleotides 12–31 in SEQ ID NO. 1); and

5' GGTTTGTGTTTTATGATACATTAC (Nucleotides 1567–1590 in SEQ. ID NO. 1)

The amplified DNA was digested with Hind III and Sal I and cloned into pDSRα2. After initial selection of transfectants in a medium containing dialyzed serum, the cells were further selected in the presence of increasing concentrations of methotrexate up to 1 βM for plasmid amplification. Selected colonies were checked for the expression of the PBSF gene by dot Northern hybridization. Conditioned medium for bioassays was generated by growing CHO (DHFR⁻) cells in serum-free DMEM for 72 hrs.

C. Expression in PA317 cells

The 1.78 kb. Hind III fragment encoding PBSF was inserted into the mpZen vector (Johnson Dev. Biol. Stand. 69, 3 (1988)) for the expression of PBSF under the myeloproliferative sarcoma virus (MPSV) promoter. Psi 2 cells (Miller et al. Biotechnique 7, 980–990 (1989)) were transfected by electroporation with mpZen containing the PBSF gene along with the plasmid SV2-Neo. Neomycin-resistant colonies were selected on G418 and RNA was dot blotted and hybridized to identify those colonies producing high levels of PBSF. Conditioned medium from a high level producer was used to infect the amphitrophic packaging cell line PA317 (Miller et al. Mol. Cell. Biol. 6, 2895–2902 (1986)) in the presence of polybrene. Conditioned medium was generated from transfected PA317 cultures for bioassays and for infections of baby mice (see below). These cells were also used for bone marrow transplantation experiments.

EXAMPLE 3

Expression of PBSF Fusion Protein and Production of Antibodies

A. E. coli fusion protein

Figure 5A:
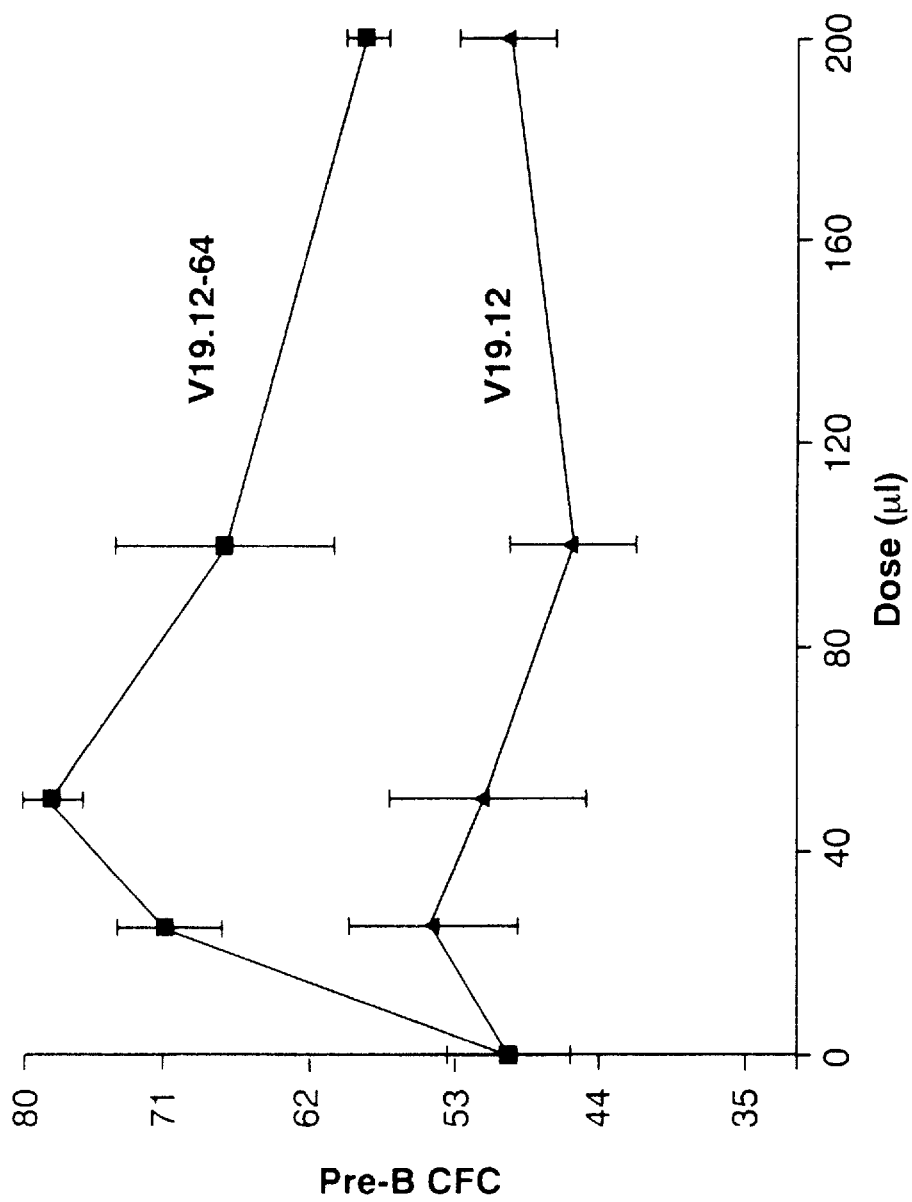
Figure 5B:
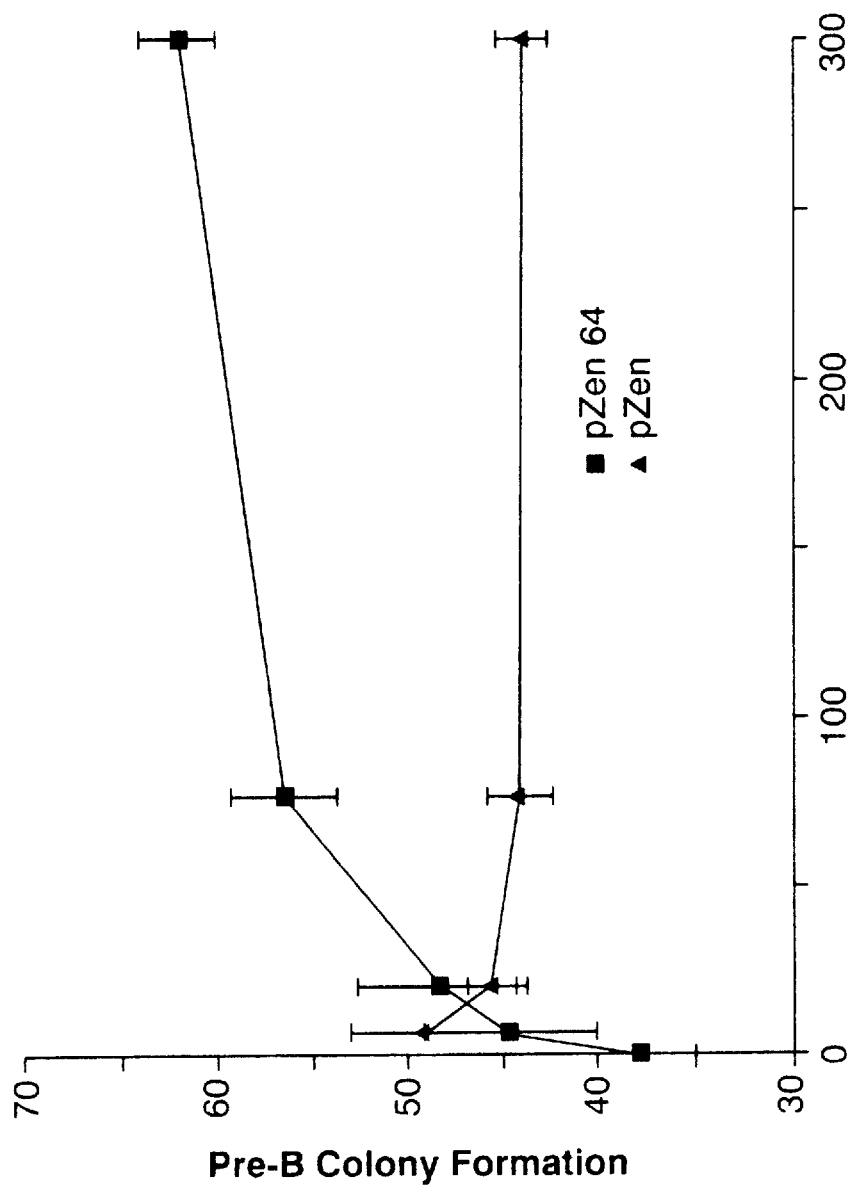

The hut 78-derived cDNA clone for PBSF was used to produce a fusion protein with either human consensus interferon or bovine growth hormone. A DNA fragment containing either the first 80 amino acids of human consensus interferon or the first 108 amino acids of bovine growth hormone was fused in frame to the P64 coding region at the Asn² residue. The consensus interferon-PBSF or bovine growth hormone-PBSF fusion proteins were expressed from the $P_L$ promoter of the plasmid pCFM 756, a modified version of pCFM736 (pCFM 736 is described in U.S. Pat. No. 4,710,473). *E. coli* FM5 was transfected with the gene encoding the fusion protein and grown at 28° C. until the OD600 was 0.3 to 0.5. The temperature was then increased to 42° C. for 2–3 hours. Emergence of inclusion bodies were visualized by light microscopy. *E. coli* cells were then lysed in Laemmli buffer and analyzed by SDS-PAGE on a 10% gel. Protein bands were visualized by Coomassie blue staining. The expression of the consensus interferon-PBSF fusion protein is shown in FIG. 3.

B. Antibody production

*E. coli* producing either a consensus interferon-PBSF or bovine growth hormone-PBSF fusion protein was grown and induced in a 500 ml batch as described above. After centrifugation, the pelleted cells were suspended in chilled water and broken by passing three times through French press at 7500 psi. After centrifugation the pelleted inclusion bodies were extracted with 5M urea to reduce the contamination of *E. coli* proteins. Fusion proteins were isolated from polyacrylamide gels as described (Hunkapiller M. et al, *Methods in Enzymol.* 91, 227–236). The gel isolated fusion proteins were lyophilized and injected to rabbits to raise antibodies. Alternatively, a PBSF peptide fragment (Cys-Arg-Glu-Lys-Lys-Thr-Glu-Asn-Ser-Lys-Leu-Arg-Lys-Val-Lys-Tyr) as set forth in SEQ ID NO. 12 was synthesized, conjugated to keyhole limpet hemocyanin (CalBiochem, La Jolla, Calif., Catalog No. 374811) and injected into rabbits to raise antibody (Liu et al. *Biochem.* 18, 690–697 (1979)).

EXAMPLE 4

Purification of PBSF

A. Purification of Rabbit Anti-PBSF antibodies and Immobilization on Cyanogen Bromide-Activated Sepharose.

Crude rabbit antibodies against the bovine growth hormone-PBSF fusion protein were purified on a Affi-gel Protein A agarose column (Bio-Rad, Richmond, Calif., Catalog No. 153–6153) using a procedure published by the manufacturer with the Affi-gel Protein A MAPS kit. The purified antibodies were coupled to cyanogen bromide activated sepharose using a procedure published as part of the IMMUNOPURE Antigen/Antibody Immobilization Kit (Pierce, Rockford, Ill., Catalog No. 44890).

B. Purification of PBSF

Conditioned medium from PA317 cells transfected with mpZEN-PBSF was the source of PBSF. The procedures used for applying sample to the antibody column and eluting PBSF from the column are those described in the IMMUNOPURE kit. After elution from the column, purified PBSF was dialyzed against PBS and was analyzed by SDS-PAGE and silver staining of the 10% gel. The results are shown in FIG. 4.

EXAMPLE 5

In Vitro Biological Activity of PBSF

Colony forming assays

Bone marrow cells obtained from normal adult Balb/c mice or mice treated previously with 5-fluorouracil (5-FU) were plated in double layer agar cultures in 35-mm dishes as previously described (Bradley et al. *J. Cell Physiol.* 94, 507 (1978)). α-modification of Eagle's MEM (Flow Labs, McLean, Va.) supplemented with 20% fetal calf serum was used for all cultures. Growth factors (SCF, IL-7 and PBSF) were incorporated in the underlays at a maximum of 13.2% of the total culture volume (1.5 ml per dish). Cultures were gassed with a 5% $O_2$,: 10% $CO_2$: 85% $N_2$ mixture and incubated for 10 to 14 days. Only colonies containing 50 or more cells were scored.

All colony forming assays were done in the presence of recombinant rat stem cell factor of 164 amino acids in length (rrSCF164) expressed in *E. coli* and purified as described in Martin et al. *Cell* 63, 203 (1990) and recombinant human IL-7 (Biosource International, Westlake, Calif.). rrSCF164 and recombinant human IL-7 were each added to a final concentration of 200 ngs/ml of culture. In FIG. 5A, assays were done to compare pre-B cell formation stimulated by conditioned medium from Cos cells transfected with either the vector 19.12 or 19.12 containing the 1.78 kb PBSF DNA fragment. In FIG. 5B, assays were done to measure pre-B cell formation by conditioned medium generated from PA317 cells carrying the PBSF gene in a retroviral vector, pZen. In FIG. 5C, purified PBSF prepared as described in Example 4 and added to bone marrow cells at the indicated volumes. The appearance of pre-B cells was verified by demonstrating that the colonies formed expressed B220 Ag and cytoplasmic $\mu$ chain but did not express surface Ig.

EXAMPLE 6

In Vivo Biological Activity of PBSF

A. Transgenic Mice

The 1.78 kb Hind III fragment carrying the PBSF gene was cloned into V19.13 which is similar to V19.12 but contains the rat albumin promoter in place of SV 40 early promoter. The DNA fragment was inserted 3' to the rat albumin promoter and enhancer. The coding sequence of the PBSF cDNA containing the albumin promoter was purified by banding on CsCl, dialyzed against 1×injection buffer (Injection buffer is 10 mM Tris, 0.1 mM EDTA, pH 7.5). 1–2 ng/$\mu$l of DNA (equivalent to about 500 copies of the linear DNA molecule) was injected per egg. The injected eggs were implanted into the pseudopregnant mice and offspring appeared 20 days later. The presence of PBSF DNA sequences in the founders was determined by PCR amplification of the DNA isolated from the tails. Blood collected from the tail bleed was analyzed on Sysmex to enumerate the white blood cell, red blood cell and platelet populations.

Founders were then inbred to generate the F1 animals, which were screened for the presence of PBSF gene. RNA isolated from the livers, bone marrow, spleen and muscle of the F1 mice were screened by reverse transcription and PCR to detect the expression of PBSF.

In order to characterize the systemic effect of PBSF expression, different organs of the F1 were isolated, fixed and cut into thin sections for histochemical analyses.

B. Retroviral Infection of Baby Mice 3 to 4 day old baby Balb/C mice were injected i.m. with 50 $\mu$l of a mixture of conditioned medium from PA317 cells transfected with either the mpZen vector, mpZen vector containing the gene encoding G-CSF, or mpZen containing the PBSF gene, and conditioned medium from NIH 3T3 cells infected with wild Moloney virus. PA317 conditioned medium and 3T3 conditioned medium were present in a ratio of 10:1 (v/v), respectively. Blood was collected in EDTA coated microfuge tubes from tail vein after intervals of 1, 2, and 3 months. Blood smear was prepared for Giemsa staining and differential counting. Sysmex analysis of the blood was carried out to enumerate the white blood cell, red blood cell and platelet population. Upon death or after euthanization, selected vital organs were removed for histological analysis.

C. Bone marrow gene transfer

B57/J mice were irradiated to destroy bone marrow cells. These mice were then transplanted with bone marrow cells from donor animals after infection in vitro by coculture for 5 days with PA317 cells harboring either the mpZen vector alone of the vector containing G-CSF or PBSF genes. After survival confirmed the successful transplantation, RNA was isolated from the blood and analyzed for the expression of respective foreign genes. Blood was then analyzed differentially by Sysmex.

EXAMPLE 7

Induction and Tissue Specificity of PBSF Expression

A. Induction of PBSF Expression

Figure 6:
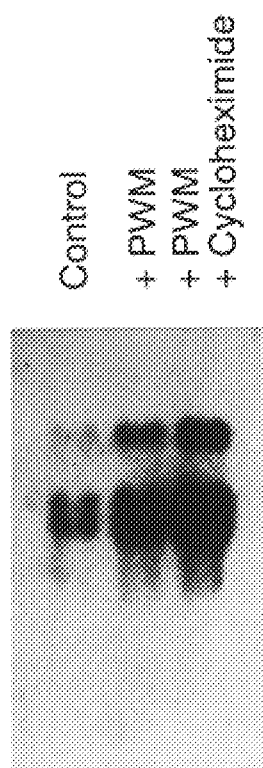
FIG. 6 shows a Northern analysis of PBSF expression in peripheral blood lymphocytes. The control lane shows expression levels in the absence of inducers for cytokine expression, the middle lane shows expression in the presence of pokeweed mitogen (PWM), the right lane shows expression in the presence of PWM and cycloheximide.

PBSF expression under various inducing conditions was studied to determine whether P64 expression could be induced under condition generally known to stimulate the synthesis of cytokines. RNA was isolated from peripheral blood lymphocytes which was untreated or treated with poke weed mitogen (PWM), or PWM and cycloheximide as described in Example 1B and 1C. RNA was electrophoresed on a 1.2% agarose gel and probed with the PBSF cDNA clone from the oligo dT primed peripheral blood lymphocyte library labelled with $^{32}$P by random priming method. The results are shown in FIG. 6.

Figure 7:
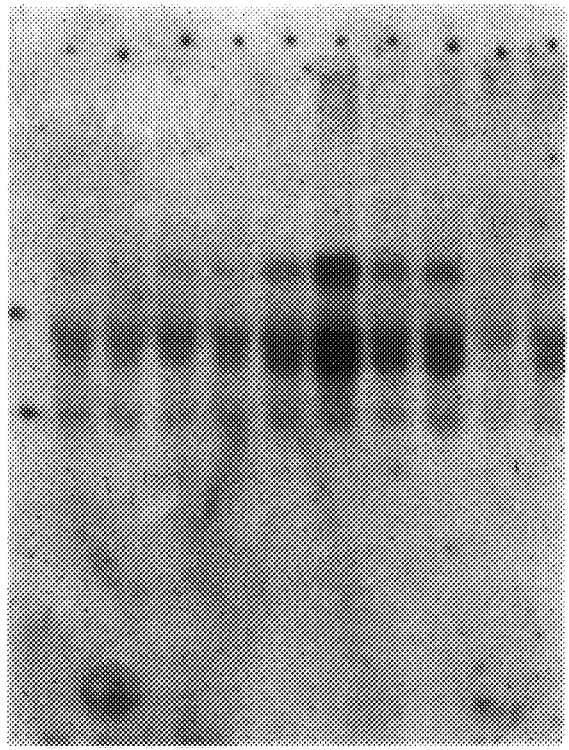
FIG. 7 shows a Northern Analysis of PBSF expression during monocytic differentiation of human leukemic cell lines. Lane 1, ML-1, untreated; Lane 2, ML-1 treated with PMA; Lane 3, ML-1 treated with tumor necrosis factor (TNF); Lane 4, ML-1 treated with TNF and IL-6; Lane 5, HL-60, untreated; Lane 6, HL-60 treated with PMA; Lane 7, HL-60 treated with TNF; Lane 8, HL-6-treated with TNF and IL-6.

The expression of PBSF during induced differentiation of human leukemic cells was also analyzed by Northern blot. Three myelomonocytic cell lines of human origin (HL-60, ATCC No. CCL-240, KG-1, ATCC No. CCL-246, and ML-1, (Samal et al. *Leuk. Res.* 14, 575–580 (1990)) were induced to differentiate towards macrophages by treatment with either PMA, tumor necrosis factor (TNF) or TNF and IL-6. RNA was isolated and subjected to a Northern analysis as described for PWM and cycloheximide induction. The results are shown in FIG. 7. The highest levels of PBSF mRNA synthesis were observed in HL-60 cells induced by PMA. Only very low levels of P64 mRNA were detected under any conditions in KG-1 and ML-1 cells.

B. Tissue specificity of PBSF Expression

Tissue specific expression of P64 was determined both by Northern analysis and RT/PCR. About 10 $\mu$g of total RNA from human brain, lungs, and placenta (all purchased from Clontech Laboratories) and 10 $\mu$g of RNA from HeLa and PMA-activated Jurkat cells were analyzed by Northern blots (Lehrach H. et al, *Biochem.* 16, 4743 (1977)) using the $^{32}$P labeled PBSF clone described in Section A as a probe. PBSF RNA was found to be present in lung tissue and in HeLa cells.

Figure 8:
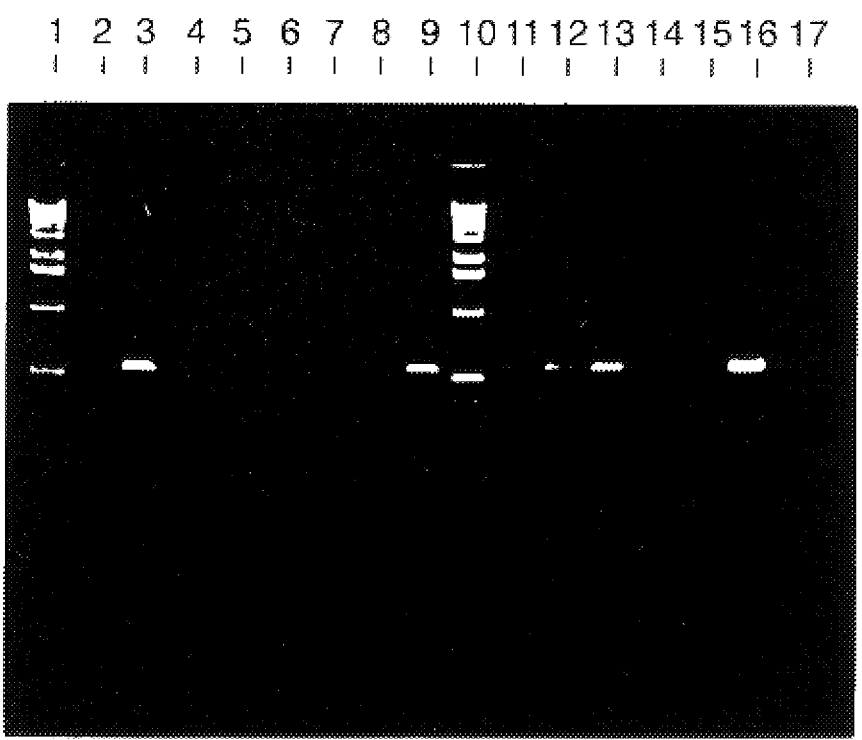
FIG. 8 shows the pattern of PBSF expression in various tissues analyzed by reverse transcriptase and PCR. Lanes 1 and 10, molecular weight markers; Lane 2, brain; Lane 3, HeLa cells; Lane 4, heart; Lane 5, skeletal muscle; Lane 6, spleen; Lane 7, pancreas; Lane 8, thymus; Lane 9, bone marrow; Lane 11, kidney; Lane 12, liver; Lane 13, lung; Lane 14, testis; Lane 15, placenta; Lane 16, peripheral blood lymphocytes; Lane 17, negative control.

Similar results were obtained using RT/PCR analysis (Noonan et al. *Nucleic Acid Res.* 16, 10366 (1988)). First strand cDNA was synthesized as described in Example 1E from about 10 $\mu$g of total RNA from HeLa cells and from human brain, heart, skeletal muscle, spleen, thymus, bone marrow, kidney, liver, lungs, testis, and placenta. PBSF mRNA was amplified by an automated thermocycler (Perkin Elmer Cetus,) using a sense primer and an antisense primer. The sense primer sequence corresponds to nucleotides 323–340 in SEQ. ID. NO. 1 and the antisense primer is complementary to nucleotides 855–872 in SEQ. ID. NO. 1. The primers were hybridized under stringent conditions for a total of 27 cycles such that the annealing temperature was about 2° C. below melting temperature ($T_m$) of the primer-template complex. The resulting primer extension products were analyzed on a 1.5% agarose gel. The results are shown in FIG. 8. PBSF mRNA was expressed in HeLa cells, bone marrow, liver and lungs and barely detectable in other tissues tested except at 40 or more cycles. The identity of the amplified products as PBSF was verified by a Southern blot analysis. A 1190 bp Hind III/Xba I subfragment of the PBSF clone labelled with $^{32}$P by random priming was used as a probe.

While the present invention has been described in terms of preferred embodiments, it is understood that variations and modifications will occur to those skilled in the art. Therefore, it is intended that the appended claims cover all such equivalent variations which come within the scope of the invention as claimed.

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 2376 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 28..1501

( x i ) SEQUENCE DESCRIPTION: SEQ ID NO:1:

```
CGCGCGGCCC CTGTCCTCCG GCCCGAG ATG AAT CCT GCG GCA GAA GCC GAG           51
                             Met Asn Pro Ala Ala Glu Ala Glu
                              1               5

TTC AAC ATC CTC CTG GCC ACC GAC TCC TAC AAG GTT ACT CAC TAT AAA         99
Phe Asn Ile Leu Leu Ala Thr Asp Ser Tyr Lys Val Thr His Tyr Lys
     10              15                  20

CAA TAT CCA CCC AAC ACA AGC AAA GTT TAT TCC TAC TTT GAA TGC CGT        147
Gln Tyr Pro Pro Asn Thr Ser Lys Val Tyr Ser Tyr Phe Glu Cys Arg
 25              30                  35                      40

GAA AAG AAG ACA GAA AAC TCC AAA TTA AGG AAG GTG AAA TAT GAG GAA        195
Glu Lys Lys Thr Glu Asn Ser Lys Leu Arg Lys Val Lys Tyr Glu Glu
                 45                  50                  55

ACA GTA TTT TAT GGG TTG CAG TAC ATT CTT AAT AAG TAC TTA AAA GGT        243
Thr Val Phe Tyr Gly Leu Gln Tyr Ile Leu Asn Lys Tyr Leu Lys Gly
             60                  65                  70

AAA GTA GTA ACC AAA GAG AAA ATC CAG GAA GCC AAA GAT GTC TAC AAA        291
Lys Val Val Thr Lys Glu Lys Ile Gln Glu Ala Lys Asp Val Tyr Lys
         75                  80                  85

GAA CAT TTC CAA GAT GAT GTC TTT AAT GAA AAG GGA TGG AAC TAC ATT        339
Glu His Phe Gln Asp Asp Val Phe Asn Glu Lys Gly Trp Asn Tyr Ile
     90                  95                 100

CTT GAG AAG TAT GAT GGG CAT CTT CCA ATA GAA ATA AAA GCT GTT CCT        387
Leu Glu Lys Tyr Asp Gly His Leu Pro Ile Glu Ile Lys Ala Val Pro
105                 110                 115                 120

GAG GGC TTT GTC ATT CCC AGA GGA AAT GTT CTC TTC ACG GTG GAA AAC        435
Glu Gly Phe Val Ile Pro Arg Gly Asn Val Leu Phe Thr Val Glu Asn
                125                 130                 135

ACA GAT CCA GAG TGT TAC TGG CTT ACA AAT TGG ATT GAG ACT ATT CTT        483
Thr Asp Pro Glu Cys Tyr Trp Leu Thr Asn Trp Ile Glu Thr Ile Leu
            140                 145                 150

GTT CAG TCC TGG TAT CCA ATC ACA GTG GCC ACA AAT TCT AGA GAG CAG        531
Val Gln Ser Trp Tyr Pro Ile Thr Val Ala Thr Asn Ser Arg Glu Gln
        155                 160                 165

AAG AAA ATA TTG GCC AAA TAT TTG TTA GAA ACT TCT GGT AAC TTA GAT        579
Lys Lys Ile Leu Ala Lys Tyr Leu Leu Glu Thr Ser Gly Asn Leu Asp
        170                 175                 180

GGT CTG GAA TAC AAG TTA CAT GAT TTT GGC TAC AGA GGA GTC TCT TCC        627
Gly Leu Glu Tyr Lys Leu His Asp Phe Gly Tyr Arg Gly Val Ser Ser
185                 190                 195                 200

CAA GAG ACT GCT GGC ATA GGA GCA TCT GCT CAC TTG GTT AAC TTC AAA        675
Gln Glu Thr Ala Gly Ile Gly Ala Ser Ala His Leu Val Asn Phe Lys
                205                 210                 215
```

| | | | | | | | | | | | | | | | | |
|---|---|---|---|---|---|---|---|---|---|---|---|---|---|---|---|---|
| GGA | ACA | GAT | ACA | GTA | GCA | GGA | CTT | GCT | CTA | ATT | AAA | AAA | TAT | TAT | GGA | 723 |
| Gly | Thr | Asp | Thr | Val | Ala | Gly | Leu | Ala | Leu | Ile | Lys | Lys | Tyr | Tyr | Gly | |
| | | | 220 | | | | 225 | | | | | | 230 | | | |
| ACG | AAA | GAT | CCT | GTT | CCA | GGC | TAT | TCT | GTT | CCA | GCA | GCA | GAA | CAC | AGT | 771 |
| Thr | Lys | Asp | Pro | Val | Pro | Gly | Tyr | Ser | Val | Pro | Ala | Ala | Glu | His | Ser | |
| | | 235 | | | | | 240 | | | | | 245 | | | | |
| ACC | ATA | ACA | GCT | TGG | GGG | AAA | GAC | CAT | GAA | AAA | GAT | GCT | TTT | GAA | CAT | 819 |
| Thr | Ile | Thr | Ala | Trp | Gly | Lys | Asp | His | Glu | Lys | Asp | Ala | Phe | Glu | His | |
| | 250 | | | | | 255 | | | | | 260 | | | | | |
| ATT | GTA | ACA | CAG | TTT | TCA | TCA | GTG | CCT | GTA | TCT | GTG | GTC | AGC | GAT | AGC | 867 |
| Ile | Val | Thr | Gln | Phe | Ser | Ser | Val | Pro | Val | Ser | Val | Val | Ser | Asp | Ser | |
| 265 | | | | | 270 | | | | | 275 | | | | | 280 | |
| TAT | GAC | ATT | TAT | AAT | GCG | TGT | GAG | AAA | ATA | TGG | GGT | GAA | GAT | CTA | AGA | 915 |
| Tyr | Asp | Ile | Tyr | Asn | Ala | Cys | Glu | Lys | Ile | Trp | Gly | Glu | Asp | Leu | Arg | |
| | | | | 285 | | | | | 290 | | | | | 295 | | |
| CAT | TTA | ATA | GTA | TCG | AGA | AGT | ACA | CAG | GCA | CCA | CTA | ATA | ATC | AGA | CCT | 963 |
| His | Leu | Ile | Val | Ser | Arg | Ser | Thr | Gln | Ala | Pro | Leu | Ile | Ile | Arg | Pro | |
| | | | 300 | | | | 305 | | | | | 310 | | | | |
| GAT | TCT | GGA | AAC | CCT | CTT | GAC | ACT | GTG | TTA | AAG | GTT | TTG | GAG | ATT | TTA | 1011 |
| Asp | Ser | Gly | Asn | Pro | Leu | Asp | Thr | Val | Leu | Lys | Val | Leu | Glu | Ile | Leu | |
| | | 315 | | | | | 320 | | | | | 325 | | | | |
| GGT | AAG | AAG | TTT | CCT | GTT | ACT | GAG | AAC | TCA | AAG | GGT | TAC | AAG | TTG | CTG | 1059 |
| Gly | Lys | Lys | Phe | Pro | Val | Thr | Glu | Asn | Ser | Lys | Gly | Tyr | Lys | Leu | Leu | |
| | 330 | | | | | 335 | | | | | 340 | | | | | |
| CCA | CCT | TAT | CTT | AGA | GTT | ATT | CAA | GGG | GAT | GGA | GTA | GAT | ATT | AAT | ACC | 1107 |
| Pro | Pro | Tyr | Leu | Arg | Val | Ile | Gln | Gly | Asp | Gly | Val | Asp | Ile | Asn | Thr | |
| 345 | | | | | 350 | | | | | 355 | | | | | 360 | |
| TTA | CAA | GAG | ATT | GTA | GAA | GGC | ATG | AAA | CAA | AAA | ATG | TGG | AGT | ATT | GAA | 1155 |
| Leu | Gln | Glu | Ile | Val | Glu | Gly | Met | Lys | Gln | Lys | Met | Trp | Ser | Ile | Glu | |
| | | | | 365 | | | | | 370 | | | | | 375 | | |
| AAT | ATT | GCC | TTC | GGT | TCT | GGT | GGA | GGT | TTG | CTA | CAG | AAG | TTG | ACA | AGA | 1203 |
| Asn | Ile | Ala | Phe | Gly | Ser | Gly | Gly | Gly | Leu | Leu | Gln | Lys | Leu | Thr | Arg | |
| | | | 380 | | | | | 385 | | | | | 390 | | | |
| GAT | CTC | TTG | AAT | TGT | TCC | TTC | AAG | TGT | AGC | TAT | GTT | GTA | ACT | AAT | GGC | 1251 |
| Asp | Leu | Leu | Asn | Cys | Ser | Phe | Lys | Cys | Ser | Tyr | Val | Val | Thr | Asn | Gly | |
| | | | 395 | | | | | 400 | | | | | 405 | | | |
| CTT | GGG | ATT | AAC | GTC | TTC | AAG | GAC | CCA | GTT | GCT | GAT | CCC | AAC | AAA | AGG | 1299 |
| Leu | Gly | Ile | Asn | Val | Phe | Lys | Asp | Pro | Val | Ala | Asp | Pro | Asn | Lys | Arg | |
| | 410 | | | | | 415 | | | | | 420 | | | | | |
| TCC | AAA | AAG | GGC | CGA | TTA | TCT | TTA | CAT | AGG | ACG | CCA | GCA | GGG | AAT | TTT | 1347 |
| Ser | Lys | Lys | Gly | Arg | Leu | Ser | Leu | His | Arg | Thr | Pro | Ala | Gly | Asn | Phe | |
| 425 | | | | | 430 | | | | | 435 | | | | | 440 | |
| GTT | ACA | CTG | GAG | GAA | GGA | AAA | GGA | GAC | CTT | GAG | GAA | TAT | GGT | CAG | GAT | 1395 |
| Val | Thr | Leu | Glu | Glu | Gly | Lys | Gly | Asp | Leu | Glu | Glu | Tyr | Gly | Gln | Asp | |
| | | | | 445 | | | | | 450 | | | | | 455 | | |
| CTT | CTC | CAT | ACT | GTC | TTC | AAG | AAT | GGC | AAG | GTG | ACA | AAA | AGC | TAT | TCA | 1443 |
| Leu | Leu | His | Thr | Val | Phe | Lys | Asn | Gly | Lys | Val | Thr | Lys | Ser | Tyr | Ser | |
| | | | 460 | | | | | 465 | | | | | 470 | | | |
| TTT | GAT | GAA | ATA | AGA | AAA | AAT | GCA | CAG | CTG | AAT | ATT | GAA | CTG | GAA | GCA | 1491 |
| Phe | Asp | Glu | Ile | Arg | Lys | Asn | Ala | Gln | Leu | Asn | Ile | Glu | Leu | Glu | Ala | |
| | | | 475 | | | | | 480 | | | | | 485 | | | |
| GCA | CAT | CAT | T AGGCTTTATG | | ACTGGGTGTG | | TGTTGTGTGT | | ATGTAATACA | | | | | | | 1541 |
| Ala | His | His | | | | | | | | | | | | | | |
| | | 490 | | | | | | | | | | | | | | |

```
TAATGTTTAT TGTACAGATG TGTGGGGTTT GTGTTTATG  ATACATTACA GCCAAATTAT    1601

TTGTTGGTTT ATGGACATAC TGCCCTTTCA TTTTTTTTCT TTTCCAGTGT TTAGGTGATC    1661

TCAAATTAGG AAATGCATTT AACCATGTAA AAGATGAGTG CTAAAGTAAG CTTTTTAGGG    1721

CCCTTTGCCA ATAGGTAGTC ATTCAATCTG GTATTGATCT TTTCACAAAT AACAGAACTG    1781
```

```
AGAAACTTTT ATATATAACT GATGATCACA TAAAACAGAT TTGCATAAAA TTACCATGAT    1841

TGCTTTATGT TTATATTTAA CTTGTATTTT TGTACAAACA AGATTGTGTA AGATATATTT    1901

GAAGTTTCAG TGATTTAACA GTCTTTCCAA CTTTTCATGA TTTTTATGAG CACAGACTTT    1961

CAAGAAAATA CTTGAAAATA AATTACATTG CCTTTTGTCC ATTAATCAGC AAATAAAACA    2021

TGGCCTTAAC AAAGTTGTTT GTGTTATTGT ACAATTTGAA AATTATGTCG GGACATACCC    2081

TATAGAATTA CTAACCTTAC TGCCCCTTGT AGAATATGTA TTAATCATTC TACATTAAAG    2141

AAAATAATGG TTCTTACTGG AATGTCTAGG CACTGTACAG TTATTATATA TCTTGGTTGT    2201

TGTATTGTAC CAGTGAAATG CCAAATTTGA AAGGCCTGTA CTGCAATTTT ATATGTCAGA    2261

GATTGCCTGT GGCTCTAATA TGCACCTCAA GATTTTAAGG AGATAATGTT TTTAGAGAGA    2321

ATTTCTGCTT CCACTATAGA ATATATACAT AAATGTAAAA TACTTACAAA AGTGG          2376
```

( 2 ) INFORMATION FOR SEQ ID NO:2:

( i ) SEQUENCE CHARACTERISTICS:
        ( A ) LENGTH: 491 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Asn Pro Ala Ala Glu Ala Glu Phe Asn Ile Leu Leu Ala Thr Asp
 1               5                  10                  15

Ser Tyr Lys Val Thr His Tyr Lys Gln Tyr Pro Pro Asn Thr Ser Lys
                 20                  25                  30

Val Tyr Ser Tyr Phe Glu Cys Arg Glu Lys Lys Thr Glu Asn Ser Lys
                 35                  40                  45

Leu Arg Lys Val Lys Tyr Glu Glu Thr Val Phe Tyr Gly Leu Gln Tyr
         50                  55                  60

Ile Leu Asn Lys Tyr Leu Lys Gly Lys Val Val Thr Lys Glu Lys Ile
 65                  70                  75                  80

Gln Glu Ala Lys Asp Val Tyr Lys Glu His Phe Gln Asp Asp Val Phe
                 85                  90                  95

Asn Glu Lys Gly Trp Asn Tyr Ile Leu Glu Lys Tyr Asp Gly His Leu
                100                 105                 110

Pro Ile Glu Ile Lys Ala Val Pro Glu Gly Phe Val Ile Pro Arg Gly
                115                 120                 125

Asn Val Leu Phe Thr Val Glu Asn Thr Asp Pro Glu Cys Tyr Trp Leu
         130                 135                 140

Thr Asn Trp Ile Glu Thr Ile Leu Val Gln Ser Trp Tyr Pro Ile Thr
145                 150                 155                 160

Val Ala Thr Asn Ser Arg Glu Gln Lys Lys Ile Leu Ala Lys Tyr Leu
                165                 170                 175

Leu Glu Thr Ser Gly Asn Leu Asp Gly Leu Glu Tyr Lys Leu His Asp
                180                 185                 190

Phe Gly Tyr Arg Gly Val Ser Ser Gln Glu Thr Ala Gly Ile Gly Ala
         195                 200                 205

Ser Ala His Leu Val Asn Phe Lys Gly Thr Asp Thr Val Ala Gly Leu
         210                 215                 220

Ala Leu Ile Lys Lys Tyr Tyr Gly Thr Lys Asp Pro Val Pro Gly Tyr
225                 230                 235                 240

Ser Val Pro Ala Ala Glu His Ser Thr Ile Thr Ala Trp Gly Lys Asp
                245                 250                 255
```

| | | | | | | | | | | | | | | |
|---|---|---|---|---|---|---|---|---|---|---|---|---|---|---|
| His | Glu | Lys | Asp 260 | Ala | Phe | Glu | His 265 | Ile | Val | Thr | Gln | Phe 270 | Ser | Val |
| Pro | Val | Ser 275 | Val | Val | Ser | Asp 280 | Ser | Tyr | Asp | Ile | Tyr 285 | Asn | Ala | Cys | Glu |
| Lys | Ile 290 | Trp | Gly | Glu | Asp 295 | Leu | Arg | His | Leu | Ile 300 | Val | Ser | Arg | Ser | Thr |
| Gln 305 | Ala | Pro | Leu | Ile 310 | Ile | Arg | Pro | Asp | Ser 315 | Gly | Asn | Pro | Leu | Asp | Thr 320 |
| Val | Leu | Lys | Val | Leu 325 | Glu | Ile | Leu | Gly | Lys 330 | Lys | Phe | Pro | Val | Thr 335 | Glu |
| Asn | Ser | Lys | Gly 340 | Tyr | Lys | Leu | Leu | Pro 345 | Pro | Tyr | Leu | Arg | Val 350 | Ile | Gln |
| Gly | Asp | Gly 355 | Val | Asp | Ile | Asn | Thr 360 | Leu | Gln | Glu | Ile | Val 365 | Glu | Gly | Met |
| Lys | Gln 370 | Lys | Met | Trp | Ser | Ile 375 | Glu | Asn | Ile | Ala | Phe 380 | Gly | Ser | Gly | Gly |
| Gly 385 | Leu | Leu | Gln | Lys | Leu 390 | Thr | Arg | Asp | Leu | Leu 395 | Asn | Cys | Ser | Phe | Lys 400 |
| Cys | Ser | Tyr | Val | Val 405 | Thr | Asn | Gly | Leu | Gly 410 | Ile | Asn | Val | Phe | Lys 415 | Asp |
| Pro | Val | Ala | Asp 420 | Pro | Asn | Lys | Arg | Ser 425 | Lys | Lys | Gly | Arg | Leu 430 | Ser | Leu |
| His | Arg | Thr 435 | Pro | Ala | Gly | Asn | Phe 440 | Val | Thr | Leu | Glu | Glu 445 | Gly | Lys | Gly |
| Asp | Leu 450 | Glu | Glu | Tyr | Gly | Gln 455 | Asp | Leu | Leu | His | Thr 460 | Val | Phe | Lys | Asn |
| Gly 465 | Lys | Val | Thr | Lys | Ser 470 | Tyr | Ser | Phe | Asp | Glu 475 | Ile | Arg | Lys | Asn | Ala 480 |
| Gln | Leu | Asn | Ile | Glu 485 | Leu | Glu | Ala | Ala | His 490 | His | | | | | |

( 2 ) INFORMATION FOR SEQ ID NO:3:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

ACTGTGGCCT GCAGCATCTC TGCACCCGCC CGCTGCCCCA GCCCC      45

( 2 ) INFORMATION FOR SEQ ID NO:4:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

CTTGCACTTG TCACAAACAG TGCACCTACT TCAAGTTCTA CAAAG      45

( 2 ) INFORMATION FOR SEQ ID NO:5:

( i ) SEQUENCE CHARACTERISTICS:
        ( A ) LENGTH: 45 base pairs ( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:5:

AACGAGGCTT ATGTGCACGA TGCACCTGTA CGATCACTGA ACTGC     45

( 2 ) INFORMATION FOR SEQ ID NO:6:

( i ) SEQUENCE CHARACTERISTICS:
( A ) LENGTH: 45 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:6:

GTGTTGCCTG CTGCCTCCCC TGCCCCAGTA CCCCCAGGAG AAGAT     45

( 2 ) INFORMATION FOR SEQ ID NO:7:

( i ) SEQUENCE CHARACTERISTICS:
( A ) LENGTH: 45 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:7:

CTGGTCCGCC CCGGACTCCA AGCTCCCATG ACCAGACAA CGCCC     45

( 2 ) INFORMATION FOR SEQ ID NO:8:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:8:

ATGTCGACMW CSVTGCMCCH RYMYSMYCMA     30

( 2 ) INFORMATION FOR SEQ ID NO:9:

( i ) SEQUENCE CHARACTERISTICS:
( A ) LENGTH: 14 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:9:

GCTTGAATTC AAGC     14

( 2 ) INFORMATION FOR SEQ ID NO:10:

( i ) SEQUENCE CHARACTERISTICS:
( A ) LENGTH: 8 base pairs
( B ) TYPE: nucleic acid
( C ) STRANDEDNESS: single
( D ) TOPOLOGY: linear ( i i ) MOLECULE TYPE: cDNA (ix) FEATURE:
    (A) NAME/KEY: misc_binding
    (B) LOCATION: complement (1..8)

(xi) SEQUENCE DESCRIPTION: SEQ ID NO:10:

CTGGAAAG  8

(2) INFORMATION FOR SEQ ID NO:11:

(i) SEQUENCE CHARACTERISTICS:
    (A) LENGTH: 13 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:11:

CTTTCCAGAC ACA  13

(2) INFORMATION FOR SEQ ID NO:12:

(i) SEQUENCE CHARACTERISTICS:
    (A) LENGTH: 16 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:12:

Cys Arg Glu Lys Lys Thr Glu Asn Ser Lys Leu Arg Lys Val Lys Tyr
1               5                   10                  15

What is claimed is:

1. A purified and isolated polypeptide having the activity of stimulating the production of pre-B cells in the presence of stem cell factor and interleukin-7, the polypeptide comprising an amino acid sequence selected from the group consisting of:
  a) SEQ ID NO: 2;
  b) amino acids 15 to 491 of SEQ ID NO: 2;
  c) amino acids 32 to 491 of SEQ ID NO: 2; and
  d) an amino acid sequence of a naturally occurring allelic variant of SEQ ID NO: 2.

2. The polypeptide of claim 1 obtained by culturing a host cell transformed or transfected with an expression vector comprising a DNA encoding the polypeptide under conditions that allow expression of the polypeptide, and isolating the polypeptide.

3. The polypeptide of claim 2 wherein the host cell is a CHO cell.

4. The polypeptide of claim 2 wherein the DNA is cDNA.

5. The polypeptide of claim 2 wherein the DNA is genomic DNA.

6. The polypeptide of claim 2 wherein the DNA is synthetic DNA.

7. The polypeptide of claim 2 wherein the expression vector is an autonomously replicating DNA plasmid or viral vector.

8. The polypeptide of claim 2 further comprising a covalently associated detectable label.

9. The polypeptide of claim 2 further comprising a covalently associated water soluble polymer.

10. The polypeptide of claim 2 further comprising a methionine residue at its amino terminus.

11. A composition comprising the polypeptide of claim 1 and a diluent, adjuvant or carrier.

* * * * *

UNITED STATES PATENT AND TRADEMARK OFFICE
CERTIFICATE OF CORRECTION

PATENT NO. : 5,874,399
DATED : February 23, 1999
INVENTOR(S) : Samal, Babru

It is certified that error appears in the above-identified patent and that said Letters Patent is hereby corrected as shown below:

Column 3, line 25, change "SEQ ID NO. 5 IL-1β, SEQ ID NO. 4 IL-2, SEQ ID NO. 7 IL-3 and SEQ ID NO. 6 IL-6" to - -IL-1β (SEQ ID NO. 5), IL-2 (SEQ ID NO. 4), IL-3 (SEQ ID NO. 7), and IL-6 (SEQ ID NO. 6) - -.

Column 3, line 48, change "analysis" to - - Analysis - -.

Column 4, line 52, change "SEQ ID NO. 1 SEQ ID NO. 2" to - - SEQ ID NO. 1 and SEQ ID NO. 2 - -.

Column 4, line 61, change "SEQ ID NO. 1 SEQ ID NO. 2" to - - SEQ ID NO. 1 and SEQ ID NO. 2 - -.

Column 11, line 17, change "80C" to - - 80°C - -.

Column 12, line 39, change "SEQ ID NO. 1 SEQ ID NO. 2" to - - SEQ ID NO. 1 and SEQ ID NO. 2 - -.

Column 13, line 25, change "BM" to - - μM - -.

Signed and Sealed this

Thirteenth Day of July, 1999

Attest:

Q. TODD DICKINSON

*Attesting Officer*   *Acting Commissioner of Patents and Trademarks*